United States Patent [19]

Murase et al.

[11] Patent Number: 5,478,812
[45] Date of Patent: Dec. 26, 1995

[54] CHROMANOL GLYCOSIDE AND METHOD FOR PRODUCTION THEREOF

[75] Inventors: Hironobu Murase; Tsutomu Kunieda, both of Gifu; Tetsuya Tsujii, Nagoya, all of Japan

[73] Assignee: CCI Corporation, Gifu, Japan

[21] Appl. No.: 195,113

[22] Filed: Feb. 10, 1994

[30] Foreign Application Priority Data

| Feb. 10, 1993 | [JP] | Japan | 5-023026 |
| Sep. 6, 1993 | [JP] | Japan | 5-221490 |
| Dec. 28, 1993 | [JP] | Japan | 5-338083 |

[51] Int. Cl.$^6$ .......... A61K 31/70; A61K 31/35; C07H 15/20; C07H 15/04
[52] U.S. Cl. .......... 514/32; 514/451; 536/4.1; 536/120
[58] Field of Search .......... 536/4.1, 6, 121.1, 536/120; 514/32, 45

[56] References Cited

FOREIGN PATENT DOCUMENTS

| 94300958 | 5/1994 | European Pat. Off. . |
| B415118 | 3/1966 | Japan . |
| 6094976 | 5/1985 | Japan . |
| 60-116643 | 6/1985 | Japan . |
| 61-21184 | 1/1986 | Japan . |
| 62-226975 | 10/1987 | Japan . |
| 62-281855 | 12/1987 | Japan . |
| 1305097 | 8/1989 | Japan . |

OTHER PUBLICATIONS

Yoshioka, T. et al., "Studies on Hindered Phenols and Analogues. V. Synthesis, Identification...", Chem. Pharm. Bull. 39(8) (1991) pp. 2124–2125.
JACS vol. 109 No. 2 (1987) Haradá et al. pp. 527–532.

*Primary Examiner*—Douglas W. Robinson
*Assistant Examiner*—Howard C. Lee
*Attorney, Agent, or Firm*—Gordon W. Hueschen

[57] ABSTRACT

This invention provides a novel chromanol glycoside which is a water soluble antioxidant excellent in heat and pH stability and production method thereof. It is a chromanol glycoside represented by the general formula (1):

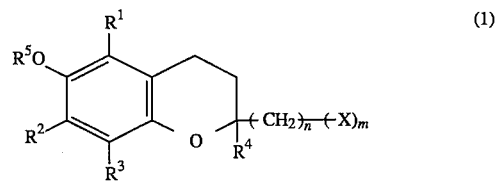

wherein $R^1$, $R^2$, $R^3$, and $R^4$ independently are a hydrogen atom or a lower alkyl group, $R^5$ is a hydrogen atom, a lower alkyl group, or a lower acyl group, X is a monosaccharide residue or an oligosaccharide residue, providing the hydrogen atom of the hydroxyl group of saccharide residue may be substituted by a lower alkyl group or a lower acyl group, n is an integer in the range of 0 to 4, and m is an integer in the range of 1 to 6.

12 Claims, 12 Drawing Sheets

CHROMANOL GLYCOSIDE AND METHOD FOR PRODUCTION THEREOF

BACKGROUND OF THE INVENTION

1. Field of the Invention

This invention relates to a novel chromanol glycoside and a method for the production thereof. More particularly, it relates to a novel water-soluble antioxidant resulting from bond of a sugar to a 2-substituted alcohol and excelling in chemical stability and to a method for the production thereof.

2. Description of the Prior Art

For a long time, the formation of lipid peroxide has been known as a cause for degradation of food in quality. It has been recently established that this substance in biological system has bearing on various diseases including arteriosclerosis, aging, and cancer, for example. Thus, the development of an antioxidant which fulfills the function of repressing the formation of lipid peroxide induced by active oxygen has been attracting growing attention not only in the field of foodstuffs but also in the field of cosmetics, the field of medicines, and many other fields.

As naturally occurring antioxidants, tocopherols, gallic acid, ascorbic acid, glutathione, and β-carotene have been known. 2(3)-tert-butyl-4-hydroxyanisole and 3,5-tert-butyl-4-hydroxytoluene which have been synthesized for the purpose of keeping foodstuffs from oxidation of lipid have been also known as antioxidants.

The tocopherols excel over the other antioxidants mentioned above in the ability to suppress oxidation. Thus, they have been finding extensive utility in the fields of foodstuffs, cosmetics, and medicines. Since this outstanding antioxidant activity of tocopherols is ascribed to the chroman ring, 6-hydroxy-2,5,7,8-tetramethyl chroman-2-carboxylic acid (hereinafter referred to as "Trolox") derived from tocopherol by the substitution of a carboxyl group for the isoprenoid side chain at the 2 position thereof has already found recognition as a commercial product. Besides, 2-substituted alcohols of tocopherols have been known.

Since the tocopherols are viscous oily substances insoluble in water, they cannot be used as solutions in the form of injections or oral medicines. Trolox and 2-substituted alcohols show extremely low solubility in water.

As means for vesting these compounds with the solubility in water, such methods as (a) addition of a surfactant, (b) coverage with cyclodextrin, and (c) chemical modification (esterification) by the use of a water-soluble compound are conceivable. The methods of (a) and (b) require a surfactant or cyclodextrin in a fairly large amount and, therefore, entail heavy adulteration of relevant compounds with an inherently extraneous substance as a serious problem. Actually these methods fail to impart fully satisfactory water solubility to the compounds (JP-A-61-21,184, JP-A-62-281,855, JP-A-62-226,975, JP-A-60-116,643, and JP-B-41-5,118). The method of (c) which consists in modifying the phenolic hydroxyl group at the 6 position with a water-soluble compound is fated to lower the antioxidant activity to a notable extent. The tocopherols and the compounds containing a chroman ring have the disadvantage of showing instability to heat and alkalis.

An object of this invention, therefore, is to provide a chromanol glycoside, a novel water-soluble antioxidant excellent in chemical stability and usable as a solution making use of the chroman ring of outstanding antioxidant activity, and a method for the production of the chromanol glycoside.

SUMMARY OF THE INVENTION

The object described above is accomplished by a chromanol glycoside represented by the general formula (1):

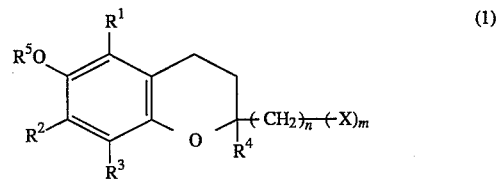

wherein $R^1$, $R^2$, $R^3$, and $R^4$ independently are a hydrogen atom or a lower alkyl group, $R^5$ is a hydrogen atom, a lower alkyl group, or a lower acyl group, X is a monosaccharide residue or an oligosaccharide residue, providing the hydrogen atom of the hydroxyl group of saccharide residue may be substituted by a lower alkyl group or a lower acyl group, n is an integer in the range of 0 to 4, and m is an integer in the range of 1 to 6.

The object is further accomplished by a method for the production of a chromanol glycoside represented by the general formula (1):

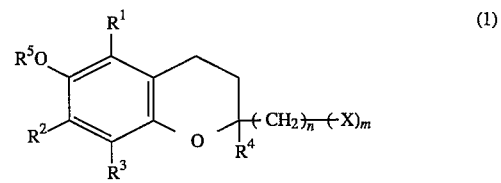

wherein $R^1$, $R^2$, $R^3$, and $R^4$ independently are a hydrogen atom or a lower alkyl group, $R^5$ is a hydrogen atom, a lower alkyl group, or a lower acyl group, X is the same meaning as defined above, n stands for an integer in the range of 0 to 4, and m is an integer in the range of 1 to 6, which method is characterized by using a 2-substituted alcohol represented by the general formula (2):

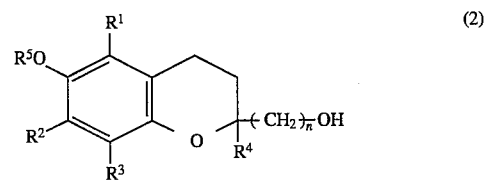

wherein $R^1$, $R^2$, $R^3$, $R^4$, and $R^5$ have the same meanings as defined above and n is the same meaning as defined above, to react with an oligosaccharide, soluble starch, starch, or cyclodextrin in the presence of an enzyme capable of catalyzing the relevant transglycosylation action.

The object is also accomplished by an antioxidant having as an effective component thereof a chromanol glycoside represented by the general formula (1):

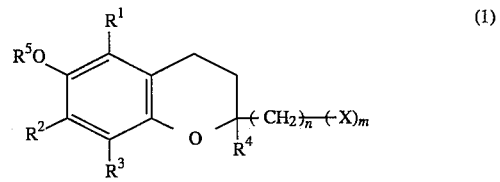

wherein $R^1$, $R^2$, $R^3$, and $R^4$ independently are a hydrogen atom or a lower alkyl group, $R^5$ is a hydrogen atom, a lower alkyl group, or a lower acyl group, X is a monosaccharide residue or an oligosaccharide residue, providing the hydrogen atom of the hydroxyl group of saccharide residue may be substituted by a lower alkyl group or a lower acyl group, n is an integer in the range of 0 to 4, and m is an integer in the range of 1 to 6.

Generally, a glycosidated substance has various advantages including (1) enhanced solubility in water, (2) enhanced chemical stability, and (3) modification and exaltation of taste and biological activity compared to unglycosidated substance. Thus, the conversion into glycoside is regarded as one of useful means for improving biologically active substances in behavior and quality. For the purpose of developing a water-soluble antioxidant containing a chroman ring, the present inventors have conceived of a novel glycoside [general formula (1)] having a sugar bound to the hydroxyl group at the 2 position of a 2-substituted alcohol [general formula (2)].

Since the chromanol glycoside according with this invention and the method for the production thereof are such as have been described above, the chromanol glycoside constitutes a novel antioxidant highly effective particularly in an aqueous solution. Because of excellent pH and thermal stability, this antioxidant proves highly useful as a raw material for cosmetic articles, articles of dress, foodstuffs, articles of formation, etc.

EXPLANATION OF THE PREFERRED EMBODIMENT

Figure 1:
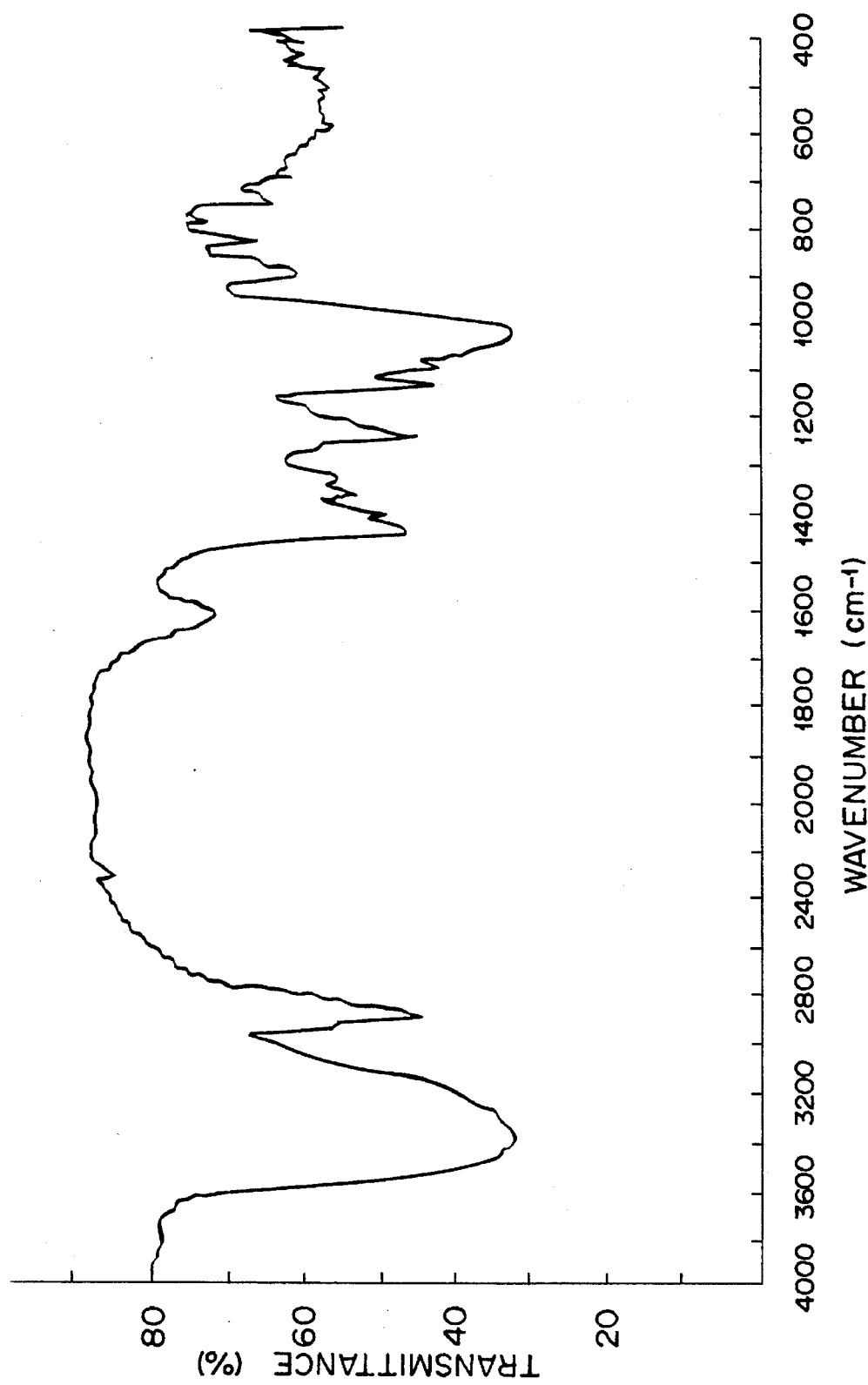
FIG. 1 is an infrared absorption spectrum of the chromanol glycoside of this invention prepared in Example 1.

The 2-substituted alcohols [general formula (2)] to be used in this invention are well-known substances and can be obtained by methods disclosed in JP-B-1-43,755 and JP-B-1-49,135, for example. The 2-substituted alcohols [general formula (2), $R^1=R^2=R^3=R^4=CH_3$, $R^5=H$, n=1] can be easily obtained by subjecting Trolox to a refluxing treatment in diethyl ether in the presence of lithium aluminum hydride.

In the above-mentioned general formula (1), m is an integer of 1 to 6, preferably 1 to 4, and n is an integer of 0 to 4, preferably 0 to 2. Further, the lower alkyl group and lower acyl group have 1 to 6, preferably 1 to 4 carbon atoms.

In the synthesis of this glycoside, it is difficult to attain by the method of chemical synthesis specifically the linkage of a specific hydroxyl group of sugar exclusively to the hydroxyl group at the 2 position of a 2-substituted alcohol [general formula (2)]. We have found a method for easily synthesizing the chromanol glycoside [general formula (1)] aimed at with high efficiency by using an enzyme. They have examined the novel chromanol glycoside produced by this method and consequently confirmed that this product excels in solubility in water and stability and exhibits an outstanding activity ideal for use in a water-soluble antioxidant. The present invention has been perfected as a result. The enzyme to be used for the synthesis is desired to be selected so as to suit the particular kind of sugar that is used in the reaction.

(1) For linkage of glucose residue by α bond to 2-substituted alcohol:

(a) The action of an α-glucosidase (EC 3.2.1.20) is desired to be used on the maltoligosaccharide at the maltotetraose position of maltose. The α-glucosidase thus used is not discriminated on account of its origin. As concrete examples of the α-glucosidase which is effectively used herein, the α-glucosidase which is produced from Saccharomyces sp. by Toyobo Co., Ltd., the α-glucosidase which is produced from *Saccharomyces cerevisiae* by Oriental Yeast Co., Ltd., the α-glucosidase which is produced from *Aspergillus niger* by Amano Pharmaceutical Co., Ltd., the α-glucosidase which is produced from Saccharomyces sp. by Wako Pure Chemical Industries Ltd., the α-glucosidase which is produced from Bakers yeast by Sigma Chemical Co., and the α-glucosidase which is produced from genus Bacillus may be cited.

(b) In the case of soluble starch or starch, the action of 4-α-D-glucanotransferase (EC 2.4.1.25) is preferable to be used.

(2) For linkage of glucose residue or maltoligosaccharide residue by α-bond to 2-substituted alcohol:

The action of cyclodextrin glucanotransferase (EC 2.4.1.19) is preferable to be used on maltoligosaccharide, soluble starch, starch, or cyclodextrin (α, β, γ). As concrete examples of this enzyme which is effectively usable herein, the cyclodextrin glucanotransferase produced from *Bacillus macerans* by Amano Pharmaceutical Co., Ltd., the cyclodextrin glucanotransferase produced from *Bacillus stearothermophilus* by Hayashibara Biochemical Laboratories, Inc., and the cyclodextrin glucanotransferases produced from *Bacillus megaterium* and from *Bacillus circulans* ATCC 9995 may be cited.

(3) For linkage of glucose residue by β-bond to 2-substituted alcohol:

(a) The action of β-glucosidase (EC 3.2.1.21) is desired to be used on the oligosaccharide formed of the β-bond such as cellobiose, Curdoran, and Laminaran.

(b) The action of cellobiose phosphorylase (EC 2.4.1.20) is preferable to be used on cellobiose in the presence of phosphoric acid.

(4) For linkage of galactose residue by α-bond to 2-substituted alcohol:

(a) The action of α-galactosidase (EC 3.2.1.22) is desired to be used on melibiose, raffinose, etc.

(5) For linkage of galactose residue by β-bond to 2-substituted alcohol:

(a) The action of β-galactosidase (EC 3.2.1.23) is desired to be used on lactose.

(b) The action of endo-1,4-β-galactanase (EC 3.2.1.89) is desired to be used on arabinogalactan, etc.

(6) Linkage of fructose residue by β-bond to 2-substituted alcohol:

(a) The action of levansucrase (EC 2.4.1.10) is desired to be used on sucrose, raffinose, melibiose, etc.

(b) The action of β-fructofuranosidase is desired to be used on sucrose.

(c) The action of inulin fructotransferase (EC 2.4.1.93) is desired to be used on inulin, etc.

In the synthesis of chromanol glycoside [general formula (1), m=1] by the use of an α-glucosidase, the reaction involved therein is preferable to use the 2-substituted alcohol [general formula (2)] as dissolved in a sugar solution. For the sake of this solution, it is preferable to add an organic solvent. As typical examples of the organic solvent which is effectively usable herein, dimethyl sulfoxide, N,N-dimethylformamide, methanol, ethanol, acetone, and acetonitrile may be cited. For the purpose of enhancing the transfer activity of α-glycosidase, dimethyl sulfoxide or N,N-dimethylformamide proves desirable. The concentration of the organic solvent used in the solution is in the range of 1 to 50 (v/v)%, preferably 5 to 35 (v/v)%.

The concentration of the 2-substituted alcohol [general formula (2)] is preferable to equal or approximate the saturated concentration thereof in the reaction solution. As respects the kind of sugar to be used, sugars of low molecular weights ranging approximately from maltose to malttetraose prove preferable. Among other sugars mentioned above, maltose proves particularly preferable. The concentration of the sugar is in the range of 1 to 70 (w/v)%, preferably 30 to 60 (w/v)%. The pH value of the reaction solution is in the range of 4.5 to 7.5, preferably 5.0 to 6.5. The reaction temperature is in the range of 10° to 70° C., preferably 30° to 60° C. The reaction time is in the range of 1 to 40 hours, preferably 2 to 24 hours. These conditions, however, are affected by the amount of the enzyme to be used in the reaction. After the reaction, the chromanol glycoside [general formula (1), m=1] of high purity is obtained by subjecting the reaction solution to column chromatography using an adsorption resin (produced by Japan Organo Co., Ltd. and marketed under trademark designation of "XAD") as a carrier.

In the synthesis of chromanol glycoside [general formula (1), m=1] by the use of cyclodextrin glucanotransferase, the reaction involved therein is preferable to use the 2-substituted alcohol [general formula (2)] as dissolved in a sugar solution. For the sake of this solution, it is desirable to add an organic solvent. As typical examples of the organic solvent which is effectively usable herein, dimethyl sulfoxide, N,N-dimethylformamide, methanol, ethanol, acetone, and acetonitrile may be cited. The concentration of the organic solvent used in the solution is in the range of 1 to 50 (v/v)%. In due consideration of the reaction efficiency, the range is preferably 5 to 35 (v/v)%. The concentration of the 2-substituted alcohol [general formula (2)] is preferable to equal or approximate the saturated concentration in the reaction solution.

The sugars which are advantageously used for the synthesis are maltoligosaccharide, soluble starch, starch, and cyclodextrin (α, β, γ) which have polymerization degrees exceeding the polymerization degree of malttriose. The concentration of the sugar is in the range of 1 to 70 (w/v) %, preferably 5 to 50 (w/v) %. The pH value is in the range of 4.5 to 8.5, preferably 5.0 to 7.5. The reaction temperature is in the range of 10° to 70° C., preferably 30° to 60° C. The reaction time is in the range of 1 to 60 hours, preferably 2 to 50 hours. These reaction conditions are affected by the amount of the enzyme to be used in the reaction.

The chromanol glycoside [general formula (1)] which is produced by the reaction is a mixture having numerals of 1 to about 8 for the variable m in the general formula. By treating this mixture with glucoamylase (EC 3.2.1.3), the chromanol glycoside [general formula (1)] having the numeral 1 exclusively for the variable m can be obtained. In this treatment, the reaction temperature is in the range of 20° to 70° C., preferably 30° to 60° C. and the reaction time in the range of 0.1 to 40 hours, preferably 1 to 24 hours. These conditions, however, are affected by the amount of the enzyme to be used. From the liquid produced by the treatment with glucoamylase, the chromanol glycoside [general formula (1), m=1] of high purity is obtained by subjecting the liquid to column chromatography using an adsorption resin (produced by Japan Organo Co., Ltd. and marketed under trademark designation of "XAD") as a carrier.

In the production of the chromanol glycoside ]general formula (1), m=2], a chromanol glycoside [general formula (1)] which has 1 and 2 exclusively for the variable m can be obtained by using β-amylase (EC 3.2.1.2) to react on the chromanol glycoside [general formula (1), m is a mixture of numerals of 1 to about 8] obtained with cyclodextrin glucanotransferase under the conditions described above. In this case, the reaction temperature is in the range of 20° to 70° C., preferably 30° to 60° C., and the reaction time in the range of 0.1 to 40 hours, preferably 1 to 24 hours. These conditions, however, are affected by the amount of the enzyme to be used. From the liquid produced by the treatment with β-amylase, the chromanol glycoside [general formula (1), m=2] of high purity is obtained and, at the same time, the chromanol glycoside [general formula (1), m=1] is obtained by subjecting the liquid to column chromatography using an adsorption resin (produced by Japan Organo Co., Ltd. and marketed under trademark designation of "XAD") as a carrier.

In the production of the chromanol glycoside [general (1), m is an integer of at least 3], a chromanol glycoside [general formula (1)] of a varying numeral of m is obtained at a high purity by subjecting the chromanol glycoside [general formula (1), m is a mixture of numerals of 1 to about 8] obtained with cyclodextrin glucanotransferase under the conditions mentioned above to fractional chromatography using HPLC.

The chromanol glycosides which are obtained as described above exhibit notably high solubility in water as compared with Trolox and 2-substituted alcohols and, therefore, can be used as solutions in the form of injections or oral medicines. These chromanol glycosides clearly excel tocopherols, Trolox, and 2-substituted alcohols in stability to withstand heat and variation of pH value.

When the chromanol glycoside was tested in a hexane isopropyl alcohol solution for the speed of peroxidation of a polyunsaturated fatty acid methyl ester for the evaluation of antioxidant activity, it was found to equal tocopherol in the antioxidant activity. When a liposome was prepared with egg yolk lecithin after the model of biomembrane and then exposed to a water-soluble radical generating agent by way of promoting a reaction of oxidation, it was found that the velocity of the oxidation was decreased by placing a chromanol glycoside in direct contact with the outer surface of the liposome. The results of the test indicate that the repression of the velocity of oxidation by the chromanol glycoside is conspicuous as compared with that obtained by ascorbic acid which is a famous water-soluble antioxidant. It is self-evident that chromanol glycosides possess an ability to erase various active oxygens including singlet oxygen because they contain a chroman ring.

Now, this invention will be described below with reference to working examples. Naturally, the scope of this invention is not limited in any sense by these working examples.

Referential Example 1

Method for determination of activity of α-glucosidase (EC 3.2.1.20)

The combination of 100 μl of an aqueous 4 (w/v) % maltose solution with 300 μl of a 100 mM phosphate buffer (pH 6.5) was incubated at 37° C. for five minutes. Then, 40 μl of an enzyme solution was added thereto and was left reacting at the same temperature for 20 minutes. The reaction solution was boiled for five minutes to stop the reaction. It was tested for glucose content with a glucose measuring kit (produced by Wako Pure Chemical Industries Ltd.). One unit of enzyme activity was defined as the amount of enzyme which hydrolyzed 1 μmol of maltose per minute under the conditions indicated above.

Referential Example 2

Method for determination of activity of cyclodextrin glucanotransferase (EC 2.4.1.19)

The amount 250 μl of an aqueous 0.55 (w/v) % soluble starch solution (produced by Merck and marketed under product code of "No. 1257") adjusted in advance with 50 mM acetate buffer solution (pH 6.0) was incubated at 40° C. for five minutes. Then 50 μl of an enzyme solution was added thereto and was left reacting at the same temperature for ten minutes. The reaction proceeding in the solution was stopped by adding 1 ml of an aqueous 0.5M acetic acid solution.

Then, the reaction solution was combined with 1 ml of an aqueous 0.02 (w/v) % $I_2$/0.2 (w/v) % KI solution and 2 ml of water and tested for absorbance at 700 nm to determine the ratio of decomposition of soluble starch. One unit of enzyme activity was defined as the amount of enzyme which decreased 10% of the absorbance at 700 nm per minutes under the same conditions indicated above.

EXAMPLE 1

Eighty (80) ml of an aqueous 60 (w/v) % maltose solution adjusted with a 50 mM phosphate buffer (pH 6.0) and 16 ml of a solution containing RS-2-substituted alcohol represented by the formula (3) at a concentration of 5 (w/v) % and 400 U of α-glucosidase (produced from Saccharomyces sp. by Toyobo Co., Ltd.) added thereto were left reacting at 40° C. for 20 hours. The conversion of the 2-substituted alcohol to a chromanol glycoside obtained at this time was about 45% in molar ratio. The reaction solution was applied to a column of an adsorption resin (produced by Japan Organo Co., Ltd. and marketed under trademark designation of "XAD-4") equilibrated in advance with a 30% methanol solution, and the column was washed with a 30% methanol solution. The chromanol glycoside was eluted with an 80% methanol solution. Then, by subjecting the chromanol glycoside fraction to silica gel column chromatography (ethyl acetate:methanol, 5:1 v/v), about 300 mg of chromanol glycoside of high purity, i.e. 6-hydroxy-2,5,7,8-tetramethyl chroman-2-methyl-α-D-glucopyranoside of the formula (4), was obtained.

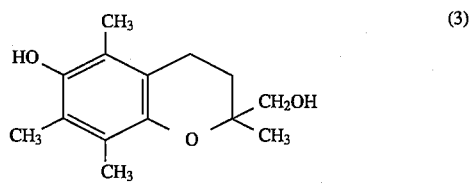
(3)

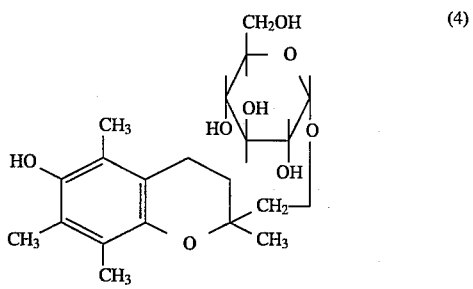
(4)

The infrared absorption spectrum of this compound is shown in FIG. 1.

This compound was subjected to $^1$H-NMR, $^{13}$C-NMR, fast atom bombardment mass spectrometry (hereinafter referred to FABMS), and specific rotation. The results are shown below.

$^1$H-NMR δ(270 MHz, DMSO-$d_6$)

1.23 and 1.25 (s, 3H)

1.69 to 1.76 (m, 1H)

1.87 to 1.92 (m, 1H)

1.97 (s, 3H)

2.02 (s, 3H)

2.04 (s, 3H)

2.51 (broad t, 2H)

3.05 to 4.88 (m, 13H)

7.39 (s, 1H)

$^{13}$C-NMR δ(67.8 MHz, DMSO-$d_6$, proton decoupling spectrum)

11.7

11.7

12.6

19.7 and 19.8

22.2 and 22.4

28.2

60.6 and 60.8

70.0 and 70.1

71.2 and 71.5

71.9

72.6 and 72.9

73.1
73.8 and 73.9
98.7 and 98.8
116.6 and 116.7
120.1 and 120.2
120.7 and 120.8
122.5
144.2
145.1
FABMS
m/z 398 (molecular ion peak)
Specific rotation
$[\alpha]^{25}_D = +85 \pm 1°$ (C=0.5, ethanol)

EXAMPLE 2

Eighty (80) ml of an aqueous 10 (w/v) % α-cyclodextrin adjusted in advance with a 50 mM acetate buffer solution (pH 6.0) and 16 ml of a solution containing RS-2-substituted alcohol of the aforementioned formula (3) at a concentration of 5 (w/v) % and adjusted with dimethyl sulfoxide and 19,000 U of cyclodextrin glucanotransferase (produced from *Bacillus stearothermophilus* by Hayashibara Biochemical Laboratories, Inc.) were left reacting at 50° C. for 43 hours. At this time, the conversion of the RS-2-substituted alcohol to a chromanol glycoside was about 95% in molar ratio. The chromanol glycoside in the reaction solution was a mixture of 1 to 8 position sugar bonds. This reaction solution was boiled for 15 minutes to inactivate the cyclodextrin glucanotransferase. The resultant solution and 400 U of glucoamylase (produced from Rhizopus sp. by Toyobo Co., Ltd.) were left reacting at 50° C. for five hours to convert not less than 95% of the chromanol glycoside in the reaction solution into a chromanol glycoside having one sugar bond. The reaction solution was boiled for ten minutes to inactivate the glucoamylase. It was then applied to a column of an adsorption resin (produced by Japan Organo Co., Ltd. and marketed under trademark designation of "XAD-4") equilibrated in advance with a 30% methanol solution, and the column was washed with a 30% methanol solution. The chromanol glycoside was eluted with an 80% methanol solution. The chromanol glycoside fraction was subjected to silica gel column chromatography (ethyl acetate:methanol, 5:1 v/v) to obtain about 1,100 mg of chromanol glycoside of high purity, i.e. 6-hydroxy-2,5,7,8-tetramethyl chroman-2-methyl-α-D-glucopyranoside represented by the aforementioned formula (4).

Figure 2:
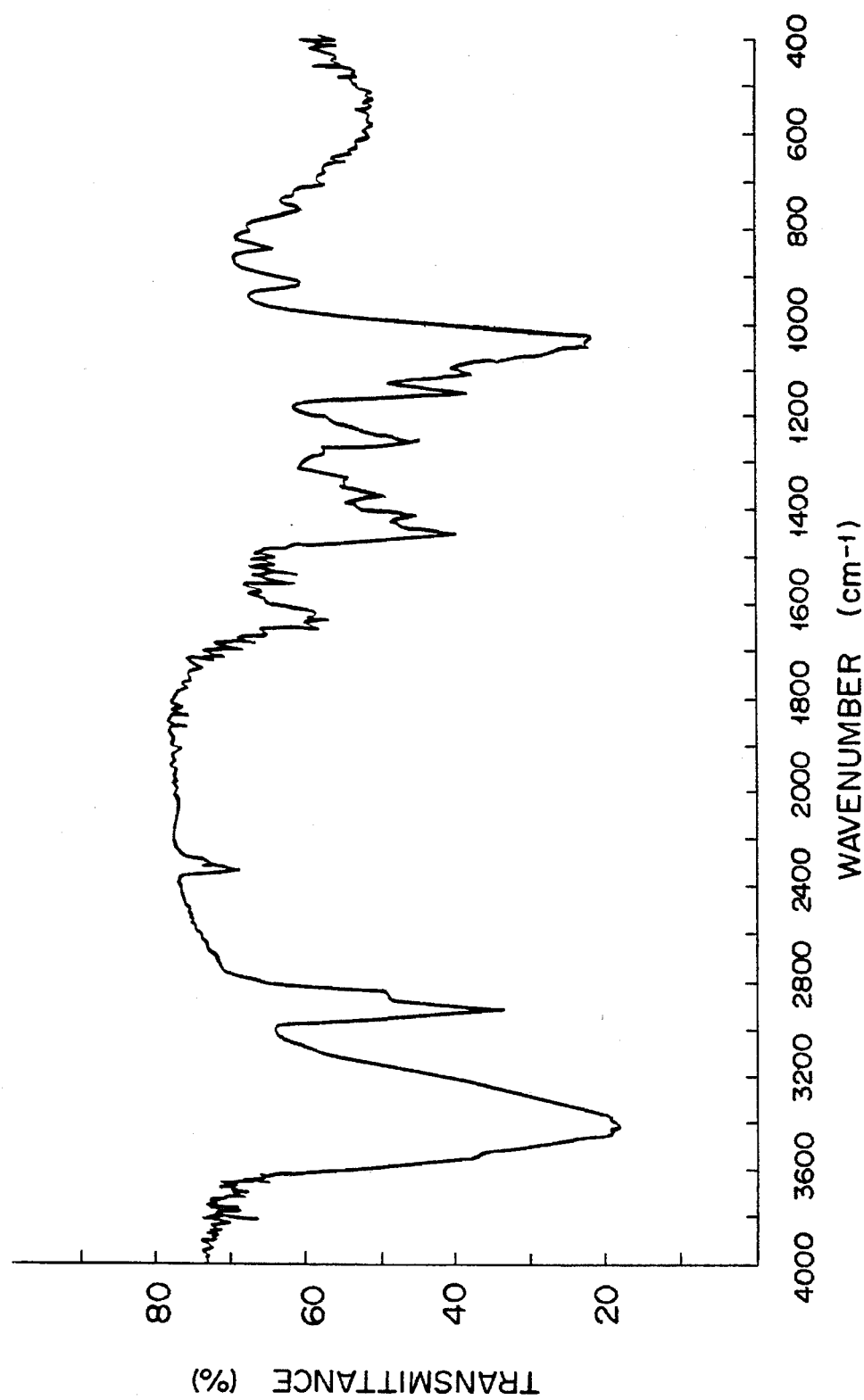
FIG. 2 is an infrared absorption spectrum of the chromanol glycoside of this invention prepared in Example 2.

The infrared absorption spectrum of this compound is shown in FIG. 2.

This compound was subjected to 1H-NMR, 13C-NMR, FABMS, and specific rotation. The results are shown below.

$^1$H-NMR δ(270 MHz, DMSO-d$_6$)

1.23 and 1.25 (s, 3H)
1.69 to 1.76 (m, 1H)
1.88 to 1.93 (m, 1H)
1.97 (s, 3H)
2.02 (s, 3H)
2.04 (s, 3H)
2.51 (broad t, 2H)
3.06 to 4.88 (m, 13H)
7.39 (s, 1H)

$^{13}$C-NMR δ(67.8 MHz, DMSO-d$_6$, proton decoupling spectrum)

11.7
11.7
12.6
19.7 and 19.9
22.2 and 22.4
28.3
60.6 and 60.8
70.0 and 70.1
71.1 and 71.4
71.9
72.6 and 72.9
73.1
73.8 and 73.9
98.8
116.6 and 116.7
120.2
120.8
122.5
144.2
145.1
FABMS
m/z 398 (molecular ion peak)
Specific rotation
$[\alpha]^{25}_D = +82 \pm 1°$ (C=0.5, ethanol)

EXAMPLE 3

The amount 120 ml of an aqueous 10 (w/v) % α-cyclodextrin solution adjusted in advance with a 50 mM acetate buffer (pH 6.0) and 24 ml of a solution containing RS-2-substituted alcohol of the aforementioned formula (3) at a concentration of 5 (w/v) % and adjusted in advance with dimethyl sulfoxide and 150,000 U of cyclodextrin glucanotransferase (produced from *Bacillus macerans* by Amano Pharmaceutical Co., Ltd.) were left reacting at 50° C. for 43 hours. At this time, the conversion of the RS-2-substituted alcohol to a chromanol glycoside was about 55% in molar ratio. The chromanol glycoside in this reaction solution was a mixture of 1 to 8 position sugar bonds. This reaction solution was boiled for 15 minutes to inactivate the cyclodextrin glucanotransferase. This solution and 600 U of glucoamylase (produced from Rhizopus sp. by Toyobo Co., Ltd. were left reacting at 50° C. for five hours to convert not less than about 95% of the chromanol glycoside in the reaction solution into a chromanol glycoside having one sugar bond. This reaction solution was boiled for ten minutes to inactivate the glucoamylase. The solution was then applied to a column of an adsorption resin (produced by Japan Organo Co., Ltd. and marketed under trademark designation of "XAD-4") equilibrated in advance with 30% methanol solution, and the column was washed with a 30% methanol solution. The chromanol glycoside was eluted with an 80% methanol solution. Then, the chromanol glycoside fraction was subjected to silica gel column chromatography (ethyl acetate:methanol, 5:1 v/v) to obtain about 950 mg of chromanol glycoside of high purity, i.e. 6-hydroxy-2,5,7,8-tetramethyl chroman-2-methyl-α-D-glucopyranoside represented by the aforementioned formula (4).

Figure 3:
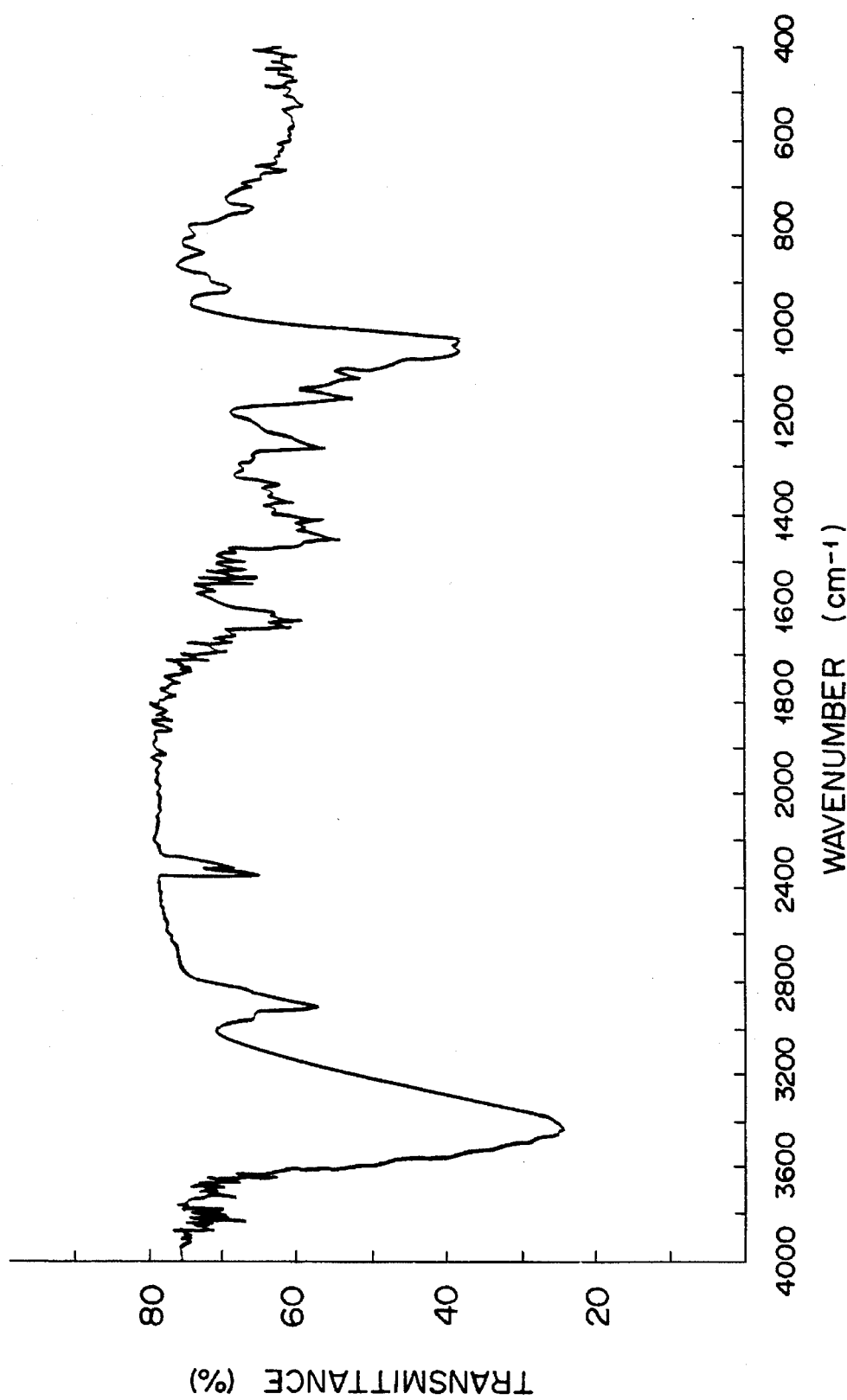
FIG. 3 is an infrared absorption spectrum of the chromanol glycoside of this invention prepared in Example 3.

The infrared absorption spectrum of this compound is shown in FIG. 3.

This compound was subjected to 1H-NMR, 13C-NMR, FABMS, and specific rotation. The results of the test are shown below.

$^1$H-NMR δ(270 MHz, DMSO-d$_6$)

1.23 and 1.25 (s, 3H)

1.69 to 1.78 (m, 1H)

1.91 to 1.93 (m, 1H)

1.97 (s, 3H)

2.02 (s, 3H)

2.04 (s, 3H)

2.51 (broad t, 2H)

3.07 to 4.88 (m, 13H)

7.40 (s, 1H)

$^{13}$C-NMR δ(67.8 MHz, DMSO-d$_6$, proton decoupling spectrum)

11.7

11.7

12.6

19.9

22.3

28.2

60.6

69.9

71.1

71.9

72.6

73.0 and 73.1

73.8

98.8

116.6 and 116.7

120.2

120.8 and 120.9

122.5

144.2

145.1

FABMS m/z 398 (molecular ion peak)

Specific rotation $[α]^{25}_D = +80 ± 1°$ (c=0.5, ethanol)

EXAMPLE 4

Eighty (80) ml of an aqueous 10 (w/v) % α-cyclodextrin solution adjusted in advance with a 50 mM acetate buffer (pH 6.0) and 16 ml of a solution containing RS-2-substituted alcohol represented by the aforementioned formula (3) at a concentration of 5 (w/v) % and adjusted in advance with dimethyl sulfoxide and 19,000 U of cyclodextrin glucanotransferase (produced from *Bacillus stearothermophilus* by Hayashibara Biochemical Laboratories, Inc.) were left reacting at 50° C. for 43 hours. At this time, the conversion of the RS-2-substituted alcohol to a chromanol glycoside was about 95% in molar ratio. The chromanol glycoside in the reaction solution was a mixture of 1 to 8 position sugar bonds. This reaction solution was boiled for 15 minutes to inactivate the cyclodextrin glucanotransferase. The solution, 70 ml of a 100 mM acetate buffer (pH 5.0) and 2,500 U of β-amylase (produced from Type I-B sweet potato by Sigma Chemical Co.) were left reacting at 50° C. for four hours. As a result, not less than about 98% of the chromanol glycoside in the reaction solution was converted into chromanol glycosides of one and two position sugar bonds. This reaction solution was boiled for ten minutes to inactivate the β-amylase. Then, the reaction solution was applied to a column of an adsorption resin (produced by Japan Organo Co., Ltd. and marketed under trademark designation of "XAD-4") equilibrated in advance with a 30% methanol solution, and the column was washed with a 30% methanol solution. The chromanol glycoside was eluted with a 80% methanol solution. The chromanol glycoside fraction consequently obtained was subjected to silica gel column chromatography (ethyl acetate:methanol, 5:1 v/v) to obtain chromanol glycosides of high purity, i.e. about 520 mg of 6-hydroxy-2,5,7,8-tetramethyl chroman-2-methyl-α-D-glucopyranoside represented by the aforementioned formula (4) and about 610 mg of 6-hydroxy-2,5,7,8-tetramethyl chroman-2-methyl-α-D-maltopyranoside represented by the formula (5).

The infrared absorption spectrum of 6-hydroxy-2,5,7,8-tetramethyl chroman-2-methyl-α-D-glucopyranoside represented by the aforementioned formula (4) is the same as shown in FIG. 2. This compound was subjected to 1H-NMR, 13C-NMR, FABMS, and specific rotation. The results of the test were identical to those obtained in Example 2.

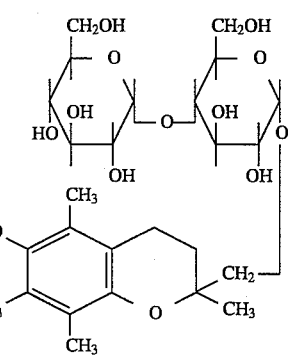

(5)

Figure 4:
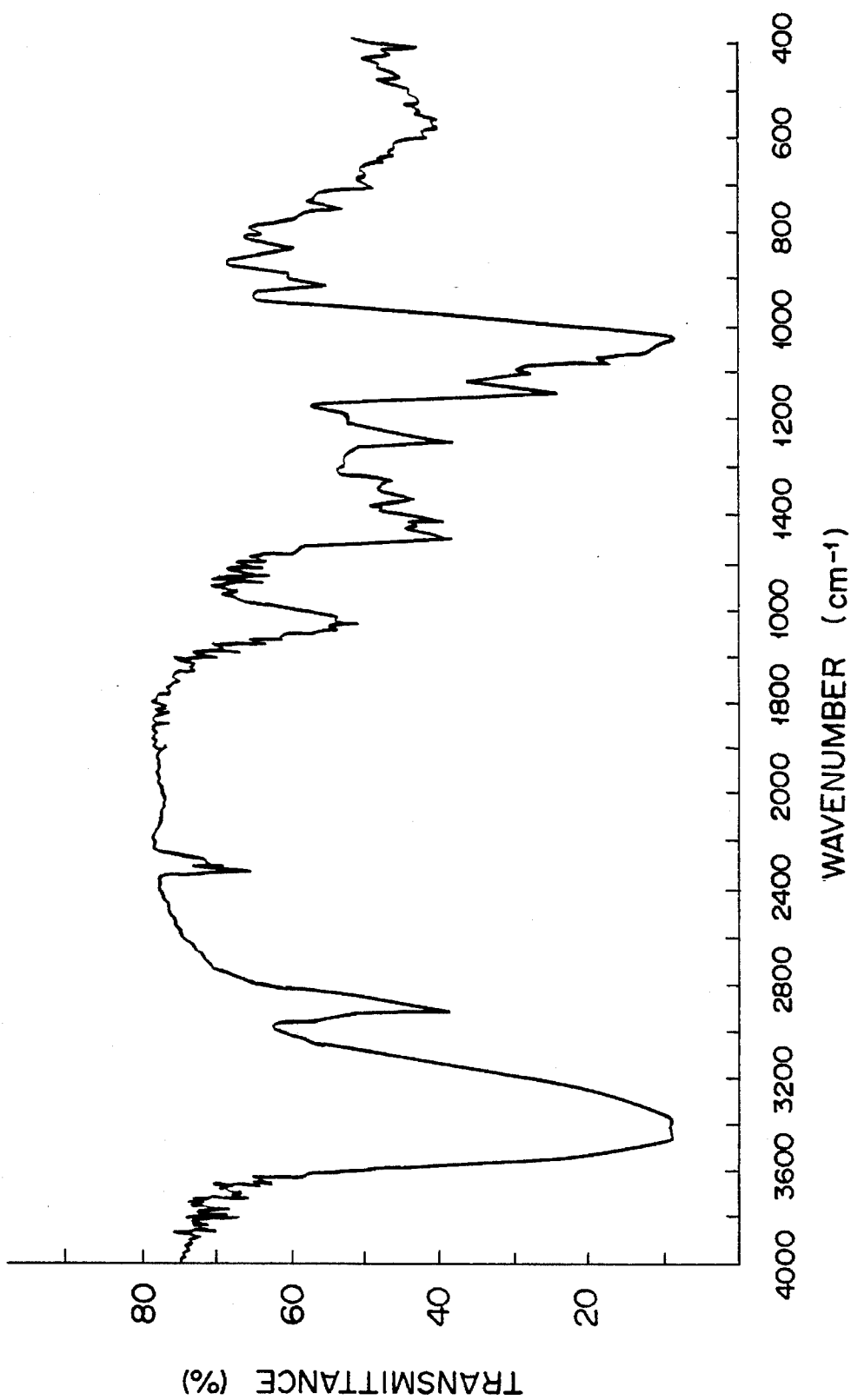
FIG. 4 is an infrared absorption spectrum of the chromanol glycoside of this invention prepared in Example 4.

The infrared absorption spectrum of the 6-hydroxy-2,5,7,8-tetramethyl chroman-2-methyl-α-D-maltopyranoside represented by the aforementioned formula (5) is shown in FIG. 4.

This compound was subjected to 1H-NMR, 13C-NMR, FABMS, and specific rotation. The results of the test are shown below.

$^1$H-NMR δ(270 MHz, DMSO-d$_6$)

1.22 and 1.25 (s, 3H)

1.69 to 1.74 (m, 1H)

1.89 (m, 1H)

1.97 (s, 3H)

2.01 (s, 3H)

2.04 (s, 3H)

2.51 (broad t, 2H)

3.09 to 5.43 (m, 23H)

7.39 (s, 1H)

$^{13}$C-NMR δ(67.8 MHz, DMSO-d$_6$, proton decoupling spectrum)

11.7

11.7

12.6

19.7 and 19.8

21.8 and 22.3

28.1 and 28.5

59.7 and 60.2

60.7

69.7

70.6 and 70.7

71.0
71.5
72.4 and 72.5
72.8 and 72.9
73.2
73.3
73.7 and 73.9
79.8
98.4 and 98.6
100.8 and 100.9
116.6
120.1 and 120.2
120.9
122.6
144.1 and 144.2
145.2
FABMS
m/z 560 (molecular ion peak)
Specific rotation
$[\alpha]^{25}{}_D = +111 \pm 1°$ (C=0.5, ethanol)

EXAMPLE 5

The amount 120 ml of an aqueous 10 (w/v) % α-cyclodextrin solution adjusted in advance with a 50 mM acetate buffer (pH 6.) and 24 ml of a solution containing RS-2-substituted alcohol represented by the aforementioned formula (3) at a concentration of 5 (w/v) % and adjusted in advance with dimethyl sulfoxide and 150,000 U of cyclodextrin glucanotransferase (produced from *Bacillus macerans* by Amano Pharmaceutical Co., Ltd.) were left reacting at 50° C. for 43 hours. At this time, the conversion of the RS-2-substituted alcohol to a chromanol glycoside was about 55% in molar ratio. The chromanol glycoside in the reaction solution was a mixture of 1 to 8 position sugar bonds. This reaction solution was boiled for 15 minutes to inactivate the cyclodextrin glucanotransferase. The reaction solution and 100 ml of a 100 mM acetate buffer (pH 5.0) and 4,000 U of β-amylase (produced from Type I-B sweet potato by SIGMA Chemical Co.) were left reacting at 50° C. for four hours. Thus, not less than about 98% of the chromanol glycoside in the reaction solution was converted into chromanol glycosides having 1 and 2 position sugar bonds. This reaction solution was boiled for ten minutes to inactivate the β-amylase. Then, the solution was applied to a column of an adsorption resin (produced by Japan Organo Co., Ltd. and marketed under trademark designation of "XAD-4") equilibrated in advance with a 30% methanol solution, and the column was washed with a 30% methanol solution. The chromanol glycoside was eluted with an 80% methanol solution. The chromanol glycoside fraction consequently obtained was subjected to silica gel column chromatography (ethyl acetate:methanol, 5:1 v/v) to obtain chromanol glycosides of high purity, i.e. about 450 mg of 6-hydroxy-2,5,7,8-tetramethyl chroman-2-methyl-α-D-glucopyranoside represented by the aforementioned formula (4) and about 440 mg of 6-hydroxy-2,5,7,8-tetramethyl chroman-2-methyl-α-D-maltopyranoside represented by the aforementioned formula (5).

The infrared absorption spectrum of the 6-hydroxy-2,5,7,8-tetramethyl chroman-2-methyl-α-D-glucopyranoside represented by the aforementioned formula (4) is the same as shown in FIG. 3. This compound was subjected to 1H-NMR, 13C-NMR, FABMS, and specific rotation. The results of the test are the same as those obtained in Example 3.

Figure 5:
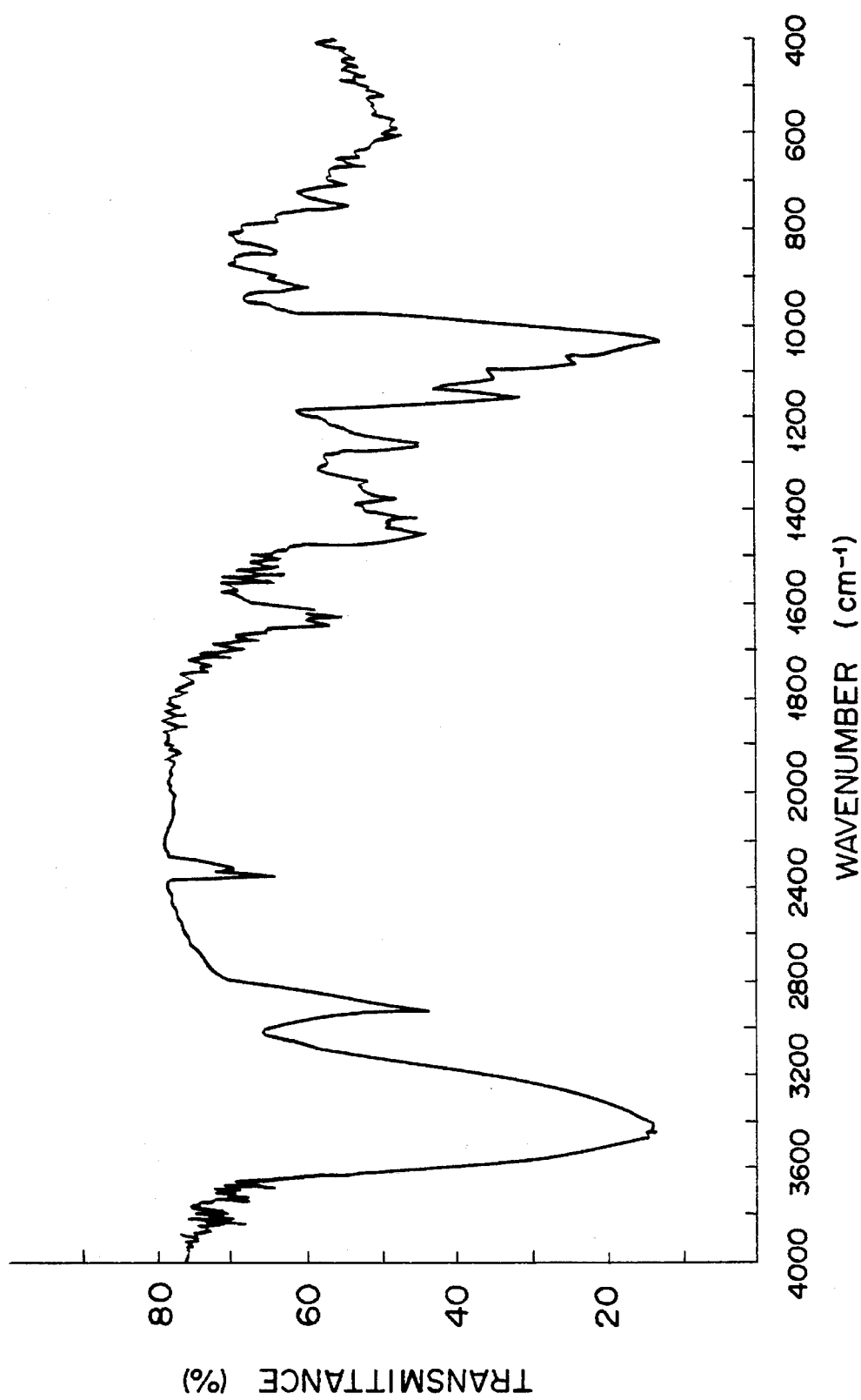
FIG. 5 is an infrared absorption spectrum of the chromanol glycoside of this invention prepared in Example 5.

The infrared absorption spectrum of the 6-hydroxy-2,5,7,8-tetramethyl chroman-2-methyl-α-D-maltopyranoside represented by the aforementioned formula (5) is shown in FIG. 5.

This compound was subjected to 1H-NMR, 13C-NMR, FABMS, and specific rotation. The results of the test are shown below.

$^1$H-NMR δ(270 MHz, DMSO-$d_6$)
1.22 and 1.26 (s, 3H)
1.75 (m, 1H)
1.89 (m, 1H)
1.97 (s, 3H)
2.02 (s, 3H)
2.03 (s, 3H)
2.50 (broad t, 2H)
3.09 to 5.43 (m, 23H)
7.39 (s, 1H)
$^{13}$C-NMR δ(67.8 MHz, DMSO-$d_6$, proton decoupling spectrum)
11.7
11.7
12.6
19.8
21.8 and 22.3
28.5
59.7
60.7
69.7
70.6 and 70.7
71.0
71.4
72.5
72.9
73.2
73.3
73.7 and 73.9
79.8
98.4 and 98.6
100.8 and 100.9
116.6
120.1 and 120.2
120.8
122.6
144.1
145.1
FABMS
m/z 560 (molecular ion peak)
Specific rotation
$[\alpha]^{25}{}_D = +113 \pm 1°$ (C=0.5, ethanol)

EXAMPLE 6

Ninety (90) ml of an aqueous 60 (w/v) % maltose solution adjusted in advance with a 50 mM phosphate buffer (pH 6.0) and 30 ml of a solution containing RS-2-substituted alcohol represented by the formula (6) at a concentration of 2.5 (w/v) % and adjusted in advance with dimethyl sulfoxide and 400 U of α-glucosidase (produced from Saccharomyces sp. by Toyobo Co., Ltd.) were left reacting at 40° C. for 20 hours. At this time, the conversion of the 2-substituted alcohol to a chromanol glycoside was about 55% in molar ratio. This reaction solution was applied to a column of an adsorption resin (produced by Japan Organo Co., Ltd. and marketed under trademark designation of "XAD-4"), and the column was washed with a 30% methanol solution. The chromanol glycoside was eluted with an 80% methanol solution. Then, the chromanol glycoside fraction was subjected to silica gel column chromatography (ethyl acetate-:methanol, 7:1, v/v) to obtain about 550 mg of a chromanol glycoside of high purity, i.e. 6-hydroxy-2,5,,7,8-tetramethyl chroman-2-ethyl-α-D-glucopyranoside represented by the formula (7).

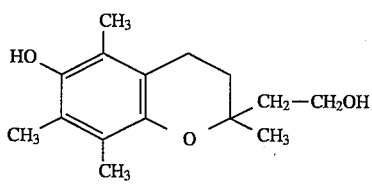
(6)

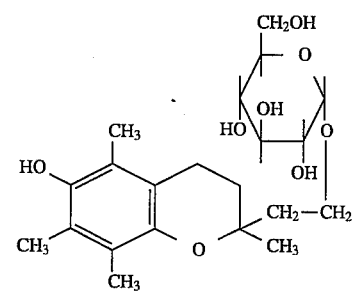
(7)

Figure 6:
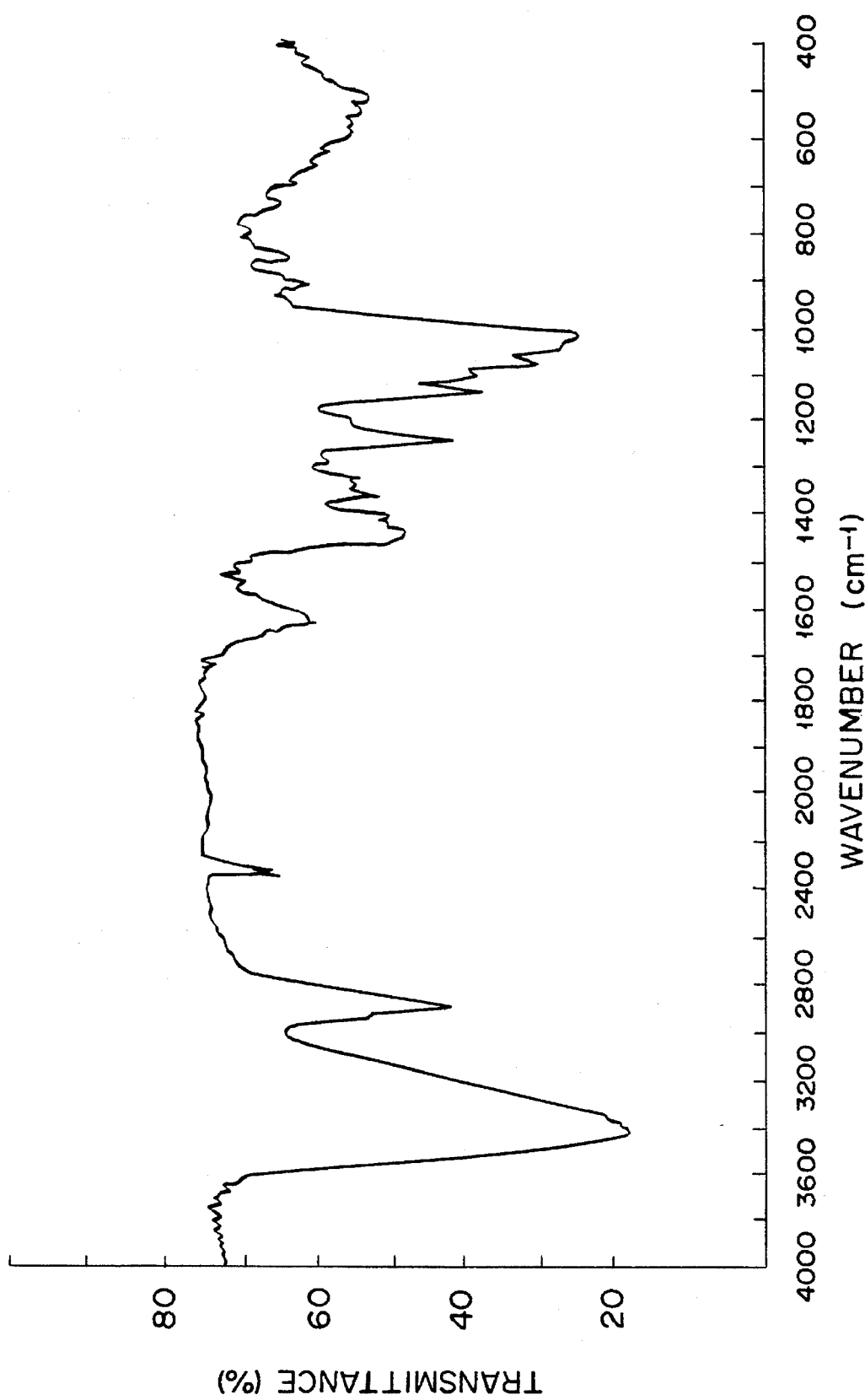
FIG. 6 is an infrared absorption spectrum of the chromanol glycoside of this invention prepared in Example 6.

The infrared absorption spectrum of this compound is shown in FIG. 6.

This compound was subjected to 1H-NMR, 13C-NMR, FABMS, and specific rotation. The results of the test are shown below.

$^1$H-NMR δ(270 MHz, DMSO-$d_6$)

1.21 and 1.22 (s, 3H)

1.76 to 1.81 (m, 4H)

1.98 (s, 3H)

2.02 (s, 3H)

2.05 (s, 3H)

2.51 (broad t, 2H)

3.03 to 4.89 (m, 13H)

7.39 (s, 1H)

$^{13}$C-NMR δ(67.8 MHz, DMSO-$d_6$, proton decoupling spectrum)

11.6

11.7

12.7

20.1

24.0 and 24.1

31.5 and 31.6

37.9 and 38.0

60.7 and 60.8

62.9 and 63.0

70.1 and 70.2

71.8

72.7 and 72.8

73.0 and 73.1

73.2

98.6 and 98.7

116.6

120.3

120.9

122.5

144.1

145.1

FABMS m/z 412 (molecular ion peak)

Specific rotation $[α]^{25}_D$=+85±1° (C=0.5, ethanol)

EXAMPLE 7

The amount 120 ml of an aqueous 10 (w/v) % α-cyclodextrin solution adjusted in advance with a 50 mM acetate buffer (pH 6.0) and 40 ml of a solution containing RS-2-substituted alcohol represented by the formula (6) at a concentration of 2.5 (w/v) % and adjusted in advance with dimethyl sulfoxide and 20,000 U of cyclodextrin glucanotransferase (produced from *Bacillus stearothermophilus* by Hayashibara Biochemical Laboratories, Inc.) were left reacting at 50° C. for 43 hours. At this time, the conversion of the RS-2-substituted alcohol to a chromanol glycoside was about 35% in molar ratio. The chromanol glycoside in the reaction solution was a mixture of 1 to 8 position sugar bonds. This reaction solution was boiled for 15 minutes to inactivate the cyclodextrin glucanotransferase. The resultant reaction solution and 600 U of glucoamylase (produced from Rhizopus sp. by Toyobo Co., Ltd. were left reacting at 50° C. for five hours to convert not less than about 95% of the chromanol glycoside in the reaction solution into a chromanol glycoside having one sugar bond. This reaction solution was boiled for 10 minutes to inactivate the glucoamylase. The solution was then applied to a column of an adsorption resin (produced by Japan Organo Co., Ltd. and marketed under trademark designation of "XAD-4") equilibrated in advance with a 30% methanol solution, and the column was washed with a 30% methanol solution. The chromanol glycoside was eluted with an 80% methanol solution. Then, the chromanol glycoside fraction was subjected to silica gel column chromatography (ethyl acetate-:methanol, 7:1 v/v) to obtain about 390 mg of a chromanol glycoside of high purity, i.e. 6-hydroxy-2,5,7,8-tetramethyl chroman-2-ethyl-α-D-glucopyranoside represented by the aforementioned formula (7).

Figure 7:
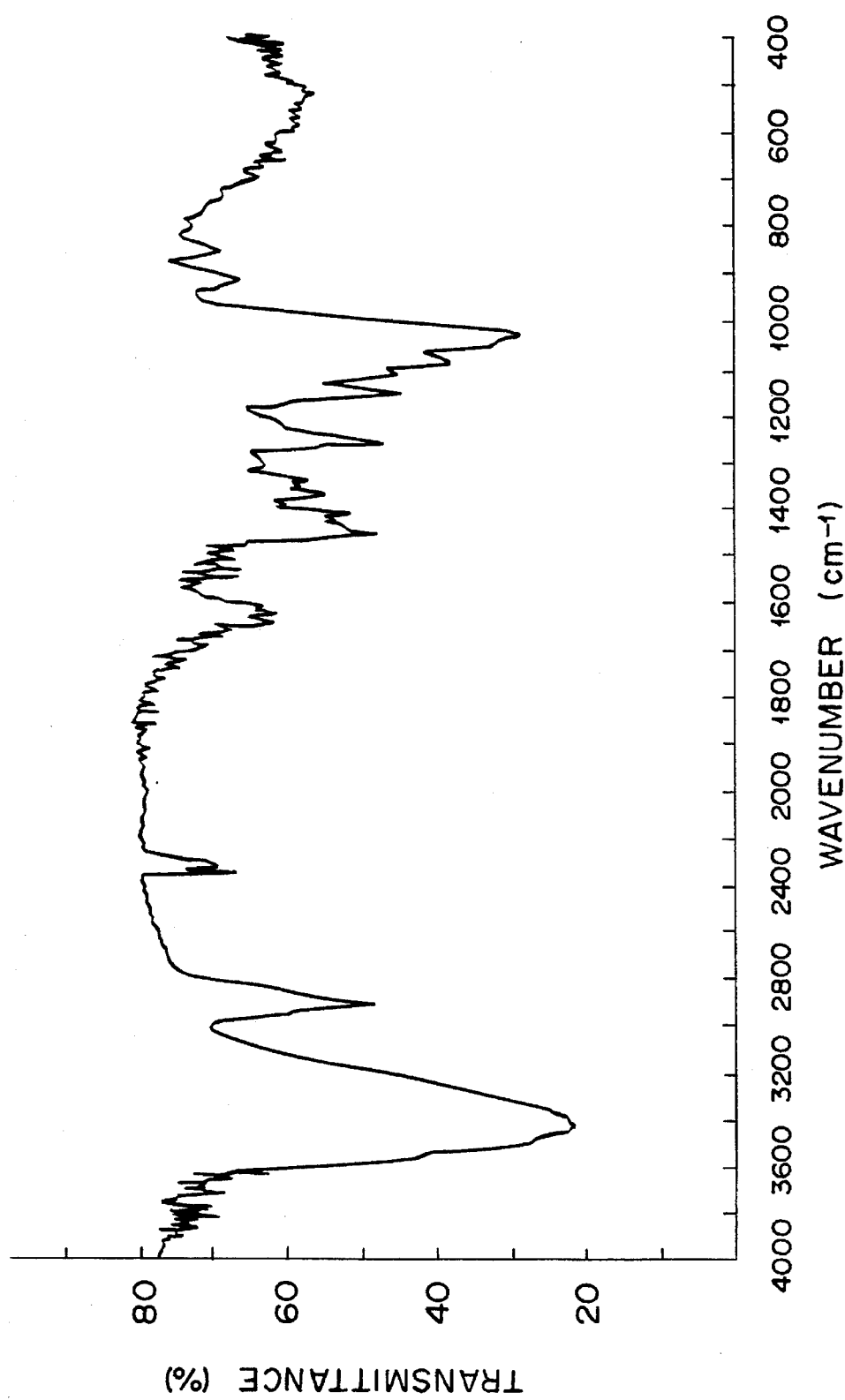
FIG. 7 is an infrared absorption spectrum of the chromanol glycoside of this invention prepared in Example 7.

The infrared absorption spectrum of this compound is shown in FIG. 7.

This compound was subjected to 1H-NMR, 13C-NMR, FABMS, and specific rotation. The results of the test are shown below.

$^1$H-NMR δ(270 MHz, DMSO-$d_6$)

1.22 (s, 3H)

1.76 to 1.81 (m, 4H)

1.98 (s, 3H)

2.01 (s, 3H)

2.05 (s, 3H)

2.51 (broad t, 2H)

3.06 to 4.86 (m, 13H)

7.38 (s, 1H)

$^{13}$C-NMR δ(67.8 MHz, DMSO-$d_6$, proton decoupling spectrum)

11.6

11.7
12.6
20.1
24.0 and 24.1
31.5 and 31.6
37.9 and 38.0
60.7 and 60.8
62.9 and 63.0
70.1
71.8
72.7 and 72.8
73.0 and 73.1
73.2
98.6 and 98.7
116.6
120.2
120.9
122.5
144.1
145.1
FABMS
m/z 412 (molecular ion peak)
Specific rotation
$[\alpha]^{25}_D = +89 \pm 1°$ (C=0.5, ethanol)

EXAMPLE 8

The amount 120 ml of an aqueous 10 (w/v) % α-cyclodextrin solution adjusted in advance with a 50 mM acetate buffer (pH 6.0) and 40 ml of a solution containing RS-2-substituted alcohol represented by the aforementioned formula (6) at a concentration of 2.5 (w/v) % and adjusted in advance with dimethyl sulfoxide and 20,000 U of cyclodextrin glucanotransferase (produced from *Bacillus stearothermophilus* by Hayashibara Biochemical Laboratories, Inc.) were left reacting at 50° C. for 43 hours. At this time, the conversion of the RS-2-substituted alcohol to a chromanol glycoside was about 35% in molar ratio. The chromanol glycoside in this reaction solution was a mixture of 1 to 8 position sugar bonds. This reaction solution was boiled for 15 minutes to inactivate the cyclodextrin glucanotransferase. The reaction solution and 110 ml of a 100 mM acetate buffer (pH 5.0) and 6,000 U of β-amylase (produced from Type B-I sweet potato by SIGMA Chemical Co.) were left reacting at 50° C. for four hours to convert not less than about 98% of the chromanol glycoside in the reaction solution into a chromanol glycoside having 1 and 2 position sugar bonds. This reaction solution was boiled for ten minutes to inactivate the β-amylase. Then, this reaction solution was applied to a column of an adsorption resin (produced by Japan Organo Co., Ltd. and marketed under trademark designation of "XAD-4") equilibrated in advance with a 30% methanol solution, and the column was washed with a 30% methanol solution. The chromanol glycoside was eluted with a 80% methanol solution. Then, the chromanol glycoside fraction was subjected to silica gel column chromatography (ethyl acetate:methanol, 7:1 v/v) to obtain chromanol glycosides of high purity, i.e. about 170 mg of 6-hydroxy-2,5,7,8-tetramethyl chroman-2-ethyl-α-D-glucopyranoside represented by the aforementioned formula (7) and about 200 mg of 6-hydroxy-2,5,7,8-tetramethyl chroman-2-ethyl-α-D-maltopyranoside represented by the formula (8).

The infrared absorption spectrum of the 6-hydroxy-2,5,7,8-tetramethyl chroman-2-ethyl-α-D-glucopyranoside represented by the aforementioned formula (7) is the same as shown in FIG. 7. This compound was subjected to $^1$H-NMR, $^{13}$C-NMR, FABMS, and specific rotation. The results of the test are identical with those of Example 7.

Figure 8:
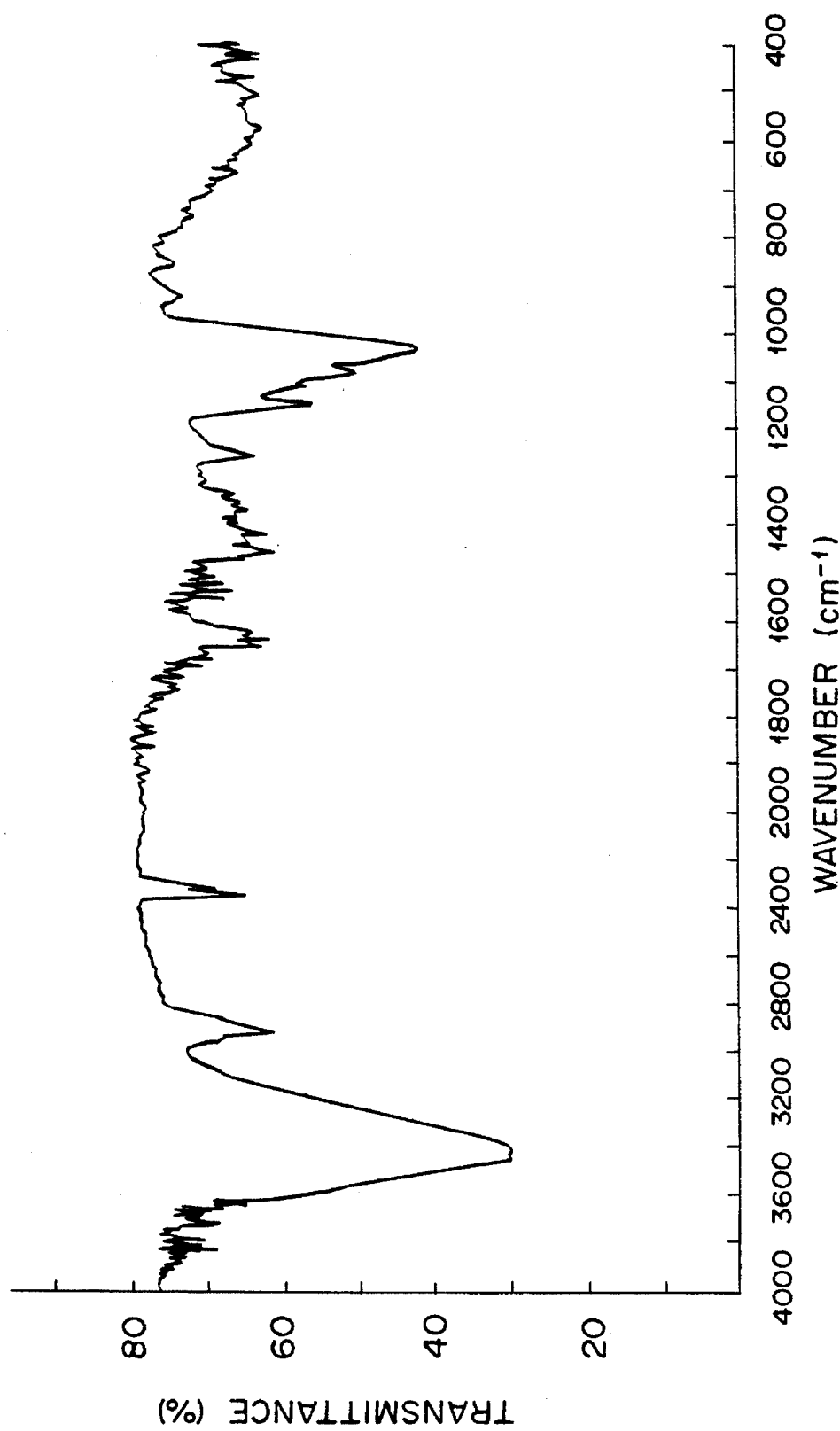
FIG. 8 is an infrared absorption spectrum of the chromanol glycoside of this invention prepared in Example 8.

The infrared absorption spectrum of the 6-hydroxy-2,5,7,8-tetramethyl chroman-2-ethyl-α-D-maltopyranoside represented by the formula (8) is shown in FIG. 8.

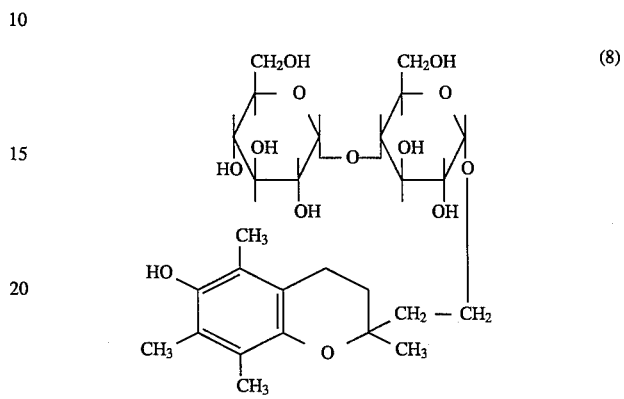

This compound was subjected to $^1$H-NMR, $^{13}$C-NMR, FABMS, and specific rotation. The results of the test are shown below.

$^1$H-NMR δ(270 MHz, DMSO-d$_6$)
1.21 (s, 3H)
1.78 to 1.85 (m, 4H)
1.98 (s, 3H)
2.01 (s, 3H)
2.05 (s, 3H)
2.50 (broad t, 2H)
3.06 to 5.41 (m, 23H)
7.38 (s, 1H)
$^{13}$C-NMR δ(67.8 MHz, DMSO-d$_6$, proton decoupling spectrum)
11.6
11.7
12.6
20.1
23.8 and 24.1
31.5
37.9 and 38.0
60.2
60.7
63.1
69.8
70.9
71.0
71.4
72.5
73.0
73.0
73.2 and 73.3
79.8
98.4
100.8
116.6
120.3

120.9
122.5
144.1
145.1
FABMS
m/z 574 (molecular ion peak)
Specific rotation
$[\alpha]^{25}D=+119°\pm1°$ (C=0.5, ethanol)

EXAMPLE 9

Figure 9:
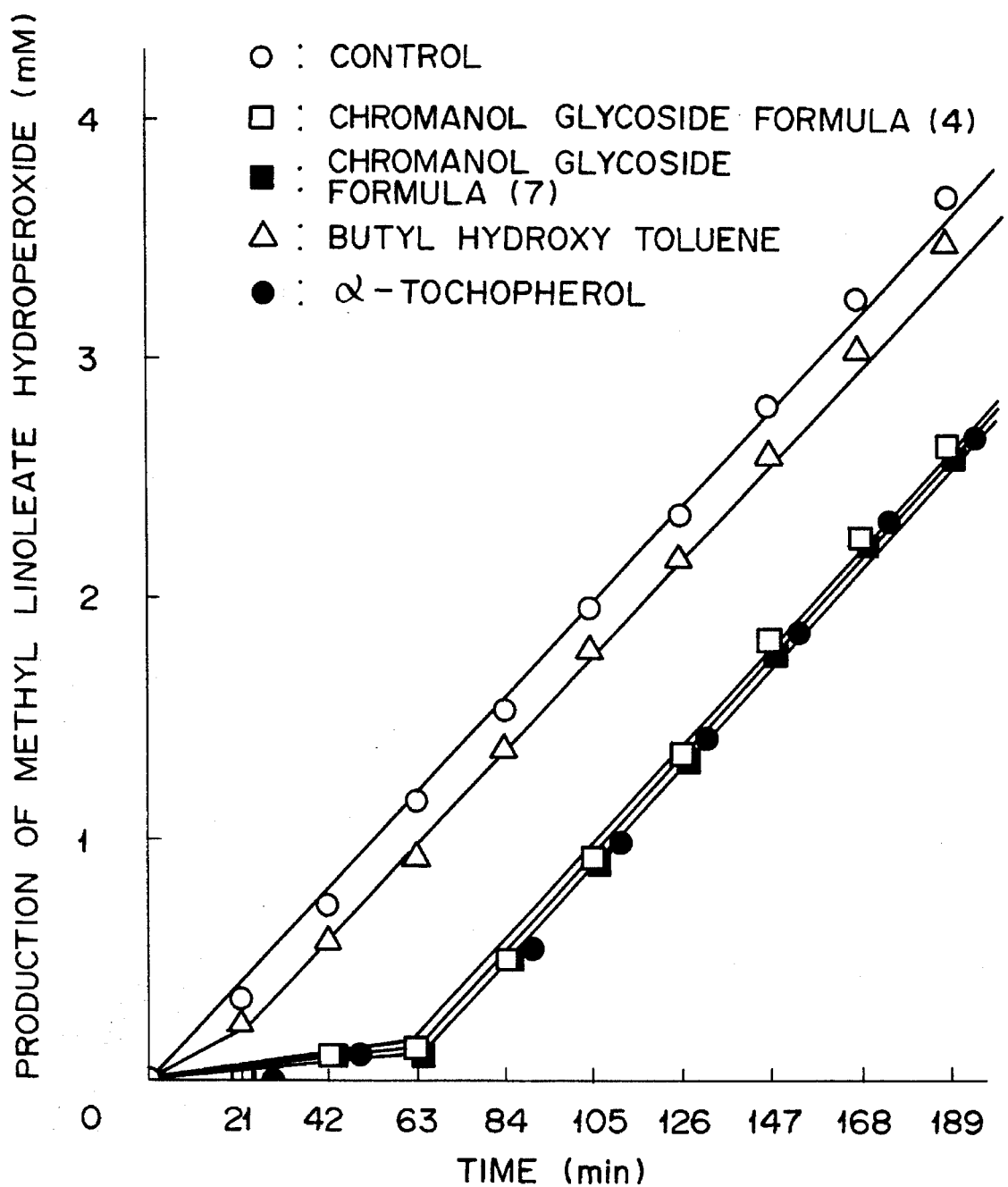
FIG. 9 is a graph showing the antioxidant activity of a chromanol glycoside according with this invention.
Figure 10:
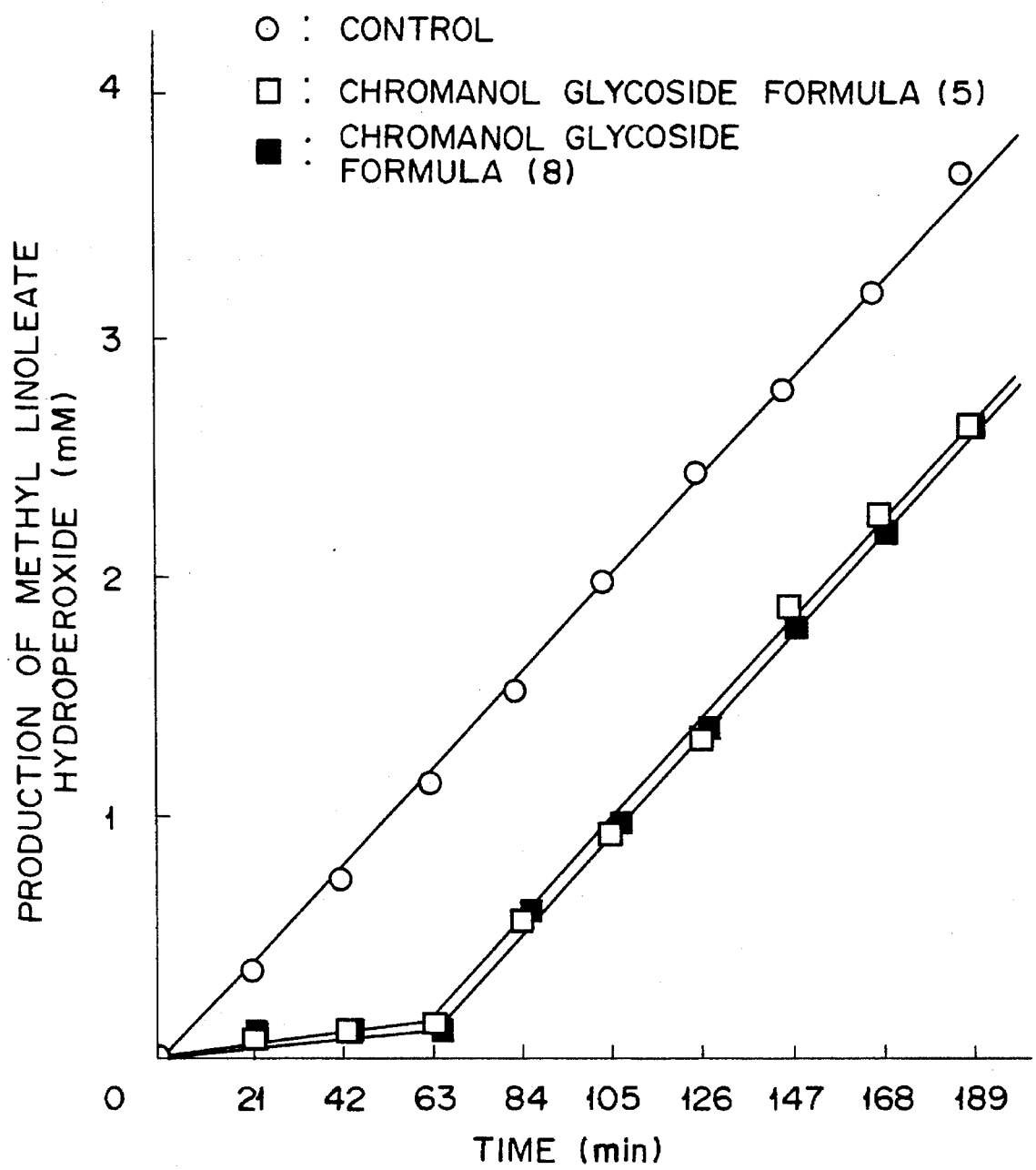
FIG. 10 is a graph showing the antioxidant activity of a chromanol glycoside according with this invention.

Antioxidant activity on the chromanol glycoside obtained in Examples 1 to 5 [6-hydroxy-2,5,7,8-tetramethyl chroman-2-methyl-α-D-glucopyranoside represented by the aforementioned formula (4)], the chromanol glycoside obtained in Examples 6 to 8 [6-hydroxy-2,5,7,8-tetramethyl chroman-2-ethyl-α-D-glucopyranoside represented by the aforementioned formula (7)], the chromanol glycoside obtained in Examples 4 and 5 [6-hydroxy-2,5,7,8-tetramethyl chroman-2-methyl-α-D-maltopyranoside represented by the aforementioned formula (5)], and the chromanol glycoside obtained in Example 8 [6-hydroxy-2,5,7,8-tetramethyl chroman-2-ethyl-α-D-maltopyranoside represented by the aforementioned formula (8)] was investigated by measuring the hydroperoxidation of methyl linoleate via radical chain reaction. Specifically, this test was performed by incubating 132 μmol of methyl linoleate, 16.5 μmol of an oil-soluble radical generator [2,2'-azo-bis(2,4-dimethyl valeronitrile)], 0.1 μmol of antioxidant in 1.1 ml of a hexane/isopropyl alcohol (1:1 v/v), and the mixture was incubated at 37° C. At regular intervals, aliquots of the reaction mixture were withdrawn and the amount of methyl linoleate hydroperoxides were measured by HPLC. The results are shown in FIGS. 9 and 10. It is clearly noted from the test results that the antioxidant activity of chromanol glycosides of the aforementioned formulas (4), (5), (7), and (8) excel 3,5-tert-butyl-4-hydroxytoluene and equal α-tocopherol in an organic solvent. EXAMPLE 10

Figure 11:
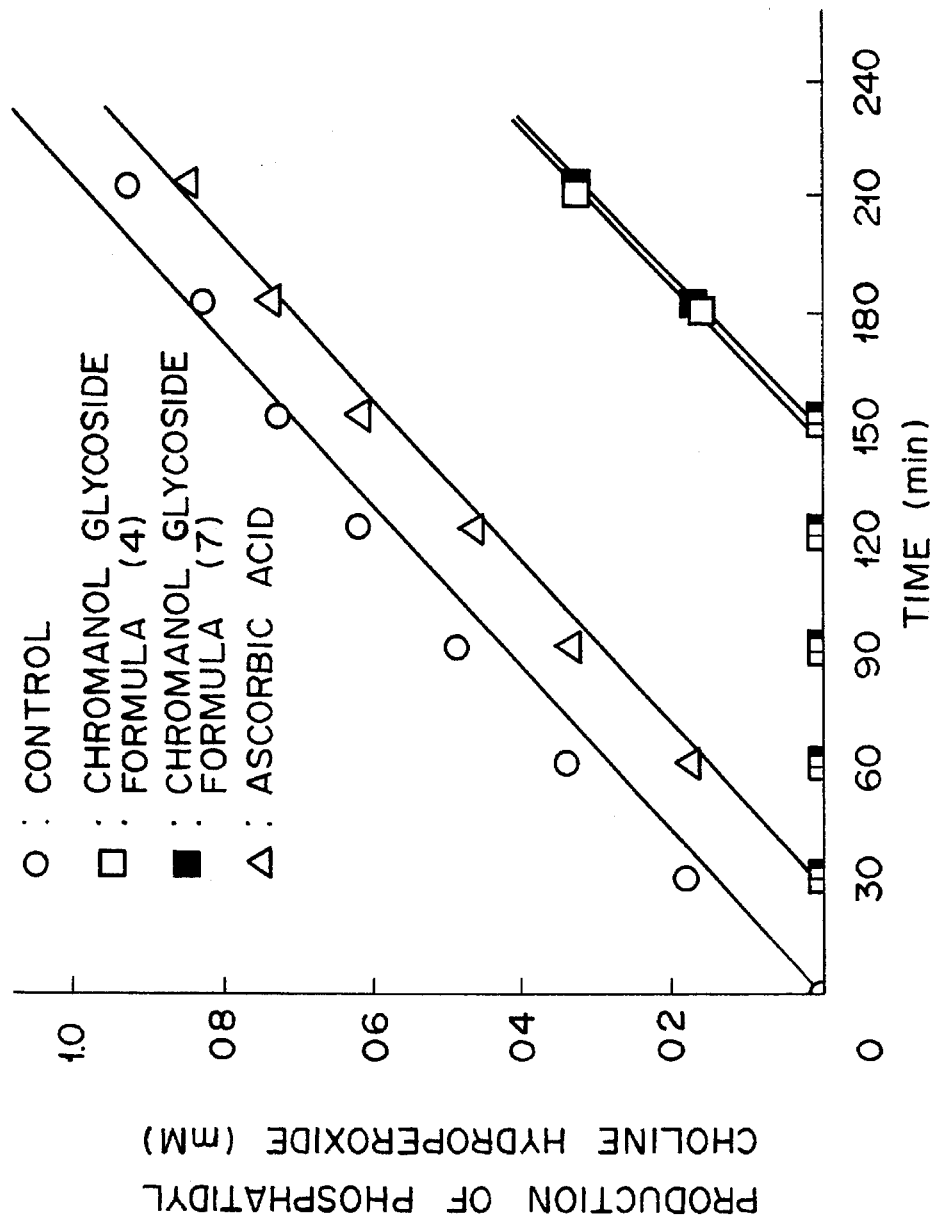
FIG. 11 is a graph showing the antioxidant activity of a chromanol glycoside according with this invention.
Figure 12:
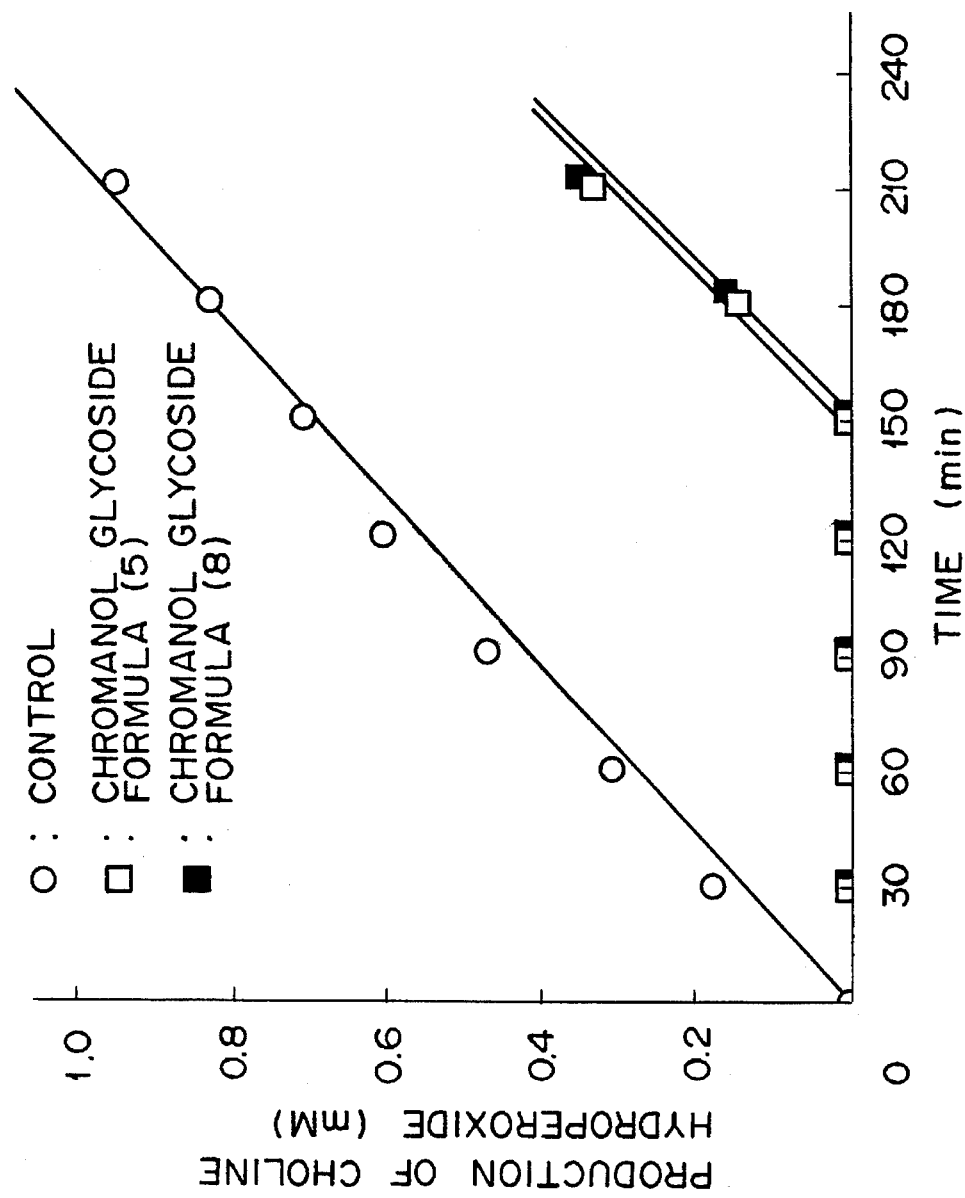
FIG. 12 is a graph showing the antioxidant activity of a chromanol glycoside according with this invention.

Antioxidant activity on the chromanol glycoside obtained in Examples 1 to 5 [6-hydroxy-2,5,7,8-tetramethyl chroman-2-methyl-α-D-glucopyranoside represented by the aforementioned formula (4)[, the chromanol glycoside obtained in Examples 6 to 8 [6-hydroxy-2,5,7,8-tetramethyl chroman-2-ethyl-α-D-glucopyranoside represented by the aforementioned formula (7)], the chromanol glycoside obtained in Examples 4 and 5 [6-hydroxy-2,5,7,8-tetramethyl chroman-2-methyl-α-D-maltopyranoside represented by the aforementioned formula (5)], and the chromanol glycoside obtained in Example 8 [6-hydroxy-2,5,7,8-tetramethyl chroman-2-ethyl-α-D-malto-pyranoside represented by the aforementioned formula (8)] was investigated by using a liposonal membranes. Specifically, this test was performed by adjusting a reaction solution consisting of 5.5 μmol of a multilameller liposomes of egg yolk phosphatidylcholine, 16.5 μmol of a water-soluble radical generator [2,2'-azo-bis(2-amidinopropane) dihydrochloride], and 0.1 μmol of antioxidant in 1.1 ml of a 10 mM tris-HCl buffer (pH 7.4). At regular intervals, aliquots of the reaction mixture were withdrawn and the amount of phosphatidylcholine hydroperoxides were measured by HPLC. The results are shown in FIGS. 11 and 12. It is clearly noted from the test results that the chromanol glycosides of the aforementioned formulas (4), (5), (7), and (8) are more effective antioxidants than ascorbic acid which is a water-soluble antioxidant.

EXAMPLE 11

The chromanol glycoside obtained in Examples 1 to 5 [6-hydroxy-2,5,7,8-tetramethyl chroman-2-methyl-α-D-glucopyranoside represented by the aforementioned formula (4)], the chromanol glycoside obtained in Examples 6 to 8 [6-hydroxy-2,5,7,8-tetramethyl chroman-2-ethyl-α-D-glucopyranoside represented by the aforementioned formula (7)], the chromanol glycoside obtained in Examples 4 and 5 [6-hydroxy-2,5,7,8-tetramethyl chroman-2methyl-α-D-maltopyranoside represented by the aforementioned formula (5)], and the chromanol glycoside obtained in Example 8 [6-hydroxy-2,5,7,8-tetramethyl chroman-2-ethyl-α-D-maltopyranoside represented by the aforementioned formula (8)] were tested for thermal stability. Specifically, this test was performed by incubating a 5 mM chromanol glycoside solution (water/ethanol, 1:3 v/v) under varying temperature conditions. At regular intervals, aliquots of the reaction mixture were withdrawn and the residual amounts of chromanol glycoside were measured by HPLC. For the purpose of comparison, the 2-substituted alcohols represented by the aforementioned formulas (3) and (6), α-tocopherol, and Trolox were similarly tested.

The results obtained after 100 hours' test are shown in Table 1 and Table 2. It is clearly noted from these test results that the conversion of 2-substituted alcohols into corresponding glycosides enhances thermal stability.

TABLE 1

|  | Temperature (°C.) | Residual amounts (%) after 100 hours |
|---|---|---|
| Chromanol glycoside of formula (4) of Example 1 | 50 | 99 |
|  | 60 | 98 |
|  | 70 | 72 |
| Chromanol glycoside of formula (4) of Example 2 | 50 | 98 |
|  | 60 | 96 |
|  | 70 | 71 |
| Chromanol glycoside of formula (4) of Example 3 | 50 | 98 |
|  | 60 | 96 |
|  | 70 | 73 |
| Chromanol glycoside of formula (4) of Example 4 | 50 | 98 |
|  | 60 | 95 |
|  | 70 | 71 |
| Chromanol glycoside of formula (4) of Example 5 | 50 | 99 |
|  | 60 | 96 |
|  | 70 | 72 |
| Chromanol glycoside of formula (7) of Example 6 | 50 | 96 |
|  | 60 | 90 |
|  | 70 | 57 |
| Chromanol glycoside of formula (7) of Example 7 | 50 | 97 |
|  | 60 | 90 |
|  | 70 | 59 |
| Chromanol glycoside of formula (7) of Example 8 | 50 | 97 |
|  | 60 | 91 |
|  | 70 | 59 |

TABLE 2

|  | Temperature (°C.) | Residual amounts (%) after 100 hours |
|---|---|---|
| Chromanol glycoside of formula (5) of Example 4 | 50 | 98 |
|  | 60 | 98 |
|  | 70 | 71 |
| Chromanol glycoside of formula (5) of Example 5 | 50 | 98 |
|  | 60 | 98 |
|  | 70 | 81 |
| Chromanol glycoside of formula (8) of Example 8 | 50 | 97 |
|  | 60 | 93 |
|  | 70 | 71 |

TABLE 2-continued

| | Temperature (°C.) | Residual amounts (%) after 100 hours |
|---|---|---|
| 2-Substituted alcohol of formula (3) | 50 | 89 |
| | 60 | 86 |
| | 70 | 60 |
| 2-Substituted alcohol of formula (6) | 50 | 92 |
| | 60 | 89 |
| | 70 | 62 |
| Trolox | 50 | 90 |
| | 60 | 82 |
| | 70 | 25 |
| α-Tocopherol | 50 | 85 |
| | 60 | 79 |
| | 70 | 30 |

EXAMPLE 12

The chromanol glycoside obtained in Examples 1 to 5 [6-hydroxy-2,5,7,8-tetramethyl chroman-2-methyl-α-D-glucopyranoside represented by the aforementioned formula (4)], the chromanol glycoside obtained in Examples 6 to 8 [6-hydroxy-2,5,7,8-tetramethyl chroman-2-ethyl-α-D-glucopyranoside represented by the aforementioned formula (7)], the chromanol glycoside obtained in Examples 4 and 5 [6-hydroxy-2,5,7,8-tetramethyl chroman-2-methyl-α-D-maltopyranoside represented by the aforementioned formula (5)], and the chromanol glycoside obtained in Example 8 [6-hydroxy-2,5,7,8-tetramethyl chroman-2-ethyl-α-D-maltopyranoside represented by the aforementioned formula (8)] were tested for pH stability. This test was specifically performed by incubating a 5.5 mM chromanol glycoside solution (buffer/ethanol, 5:1 v/v) having a varying pH value. At regular intervals, aliquots of the reaction mixture were withdrawn and the residual amounts of chromanol glycoside were measured by HPC. For the purpose of comparison, the 2-substituted alcohols represented by the aforementioned formulas (3) and (6) and Trolox were similarly tested.

The results obtained after 100 hours' test are shown in Tables 3 and 4. It is clearly noted from the test results that the conversion of 2-substituted alcohols into respective glycosides enhances pH stability. The buffer used for the test were 100 mM acetate buffer of pH 5.5, 100 mM phosphate buffer of pH 7.0, and 100 mM tris-HCl buffer of pH 8,5.

TABLE 3

| | pH | Residual amounts (%) after 100 hours |
|---|---|---|
| Chromanol glycoside of formula (4) of Example 1 | 5.5 | 91 |
| | 7.0 | 41 |
| | 8.5 | 20 |
| Chromanol glycoside of formula (4) of Example 2 | 5.5 | 85 |
| | 7.0 | 42 |
| | 8.5 | 19 |
| Chromanol glycoside of formula (4) of Example 3 | 5.5 | 89 |
| | 7.0 | 43 |
| | 8.5 | 20 |
| Chromanol glycoside of formula (4) of Example 4 | 5.5 | 84 |
| | 7.0 | 44 |
| | 8.5 | 19 |
| Chromanol glycoside of formula (4) of Example 5 | 5.5 | 88 |
| | 7.0 | 43 |
| | 8.5 | 21 |
| Chromanol glycoside of formula (7) of Example 6 | 5.5 | 69 |
| | 7.0 | 24 |
| | 8.5 | 7 |

TABLE 3-continued

| | pH | Residual amounts (%) after 100 hours |
|---|---|---|
| Chromanol glycoside of formula (7) of Example 7 | 5.5 | 71 |
| | 7.0 | 26 |
| | 8.5 | 7 |
| Chromanol glycoside of formula (7) of Example 8 | 5.5 | 70 |
| | 7.0 | 25 |
| | 8.5 | 8 |

TABLE 4

| | pH | Residual amounts (%) after 100 hours |
|---|---|---|
| Chromanol glycoside of formula (5) of Example 4 | 5.5 | 84 |
| | 7.0 | 40 |
| | 8.5 | 19 |
| Chromanol glycoside of formula (5) of Example 5 | 5.5 | 86 |
| | 7.0 | 44 |
| | 8.5 | 20 |
| Chromanol glycoside of formula (8) of Example 8 | 5.5 | 57 |
| | 7.0 | 16 |
| | 8.5 | 2 |
| 2-Substituted alcohol of formula (3) | 5.5 | 73 |
| | 7.0 | 29 |
| | 8.5 | 7 |
| 2-Substituted alcohol of formula (6) | 5.5 | 63 |
| | 7.0 | 19 |
| | 8.5 | 3 |
| Trolox | 5.5 | 75 |
| | 7.0 | 35 |
| | 8.5 | 13 |

EXAMPLE 13

The chromanol glycoside obtained in Examples 1 to 5 [6-hydroxy-2,5,7,8-tetramethyl chroman-2-methyl-α-D-glucopyranoside represented by the aforementioned formula (4)], the chromanol glycoside obtained in Examples 6 to 8 [6-hydroxy-2,5,7,8-tetramethyl chroman-2-ethyl-α-D-glucopyranoside represented by the aforementioned formula (7)], the chromanol glycoside obtained in Examples 4 and 5 [6-hydroxy-2,5,7,8-tetramethyl chroman-2-methyl-α-D-maltopyranoside represented by the aforementioned formula (5)], and the chromanol glycoside obtained in Example 8 [6-hydroxy-2,5,7,8-tetramethyl chroman-2-ethyl-α-D-maltopyranoside represented by the aforementioned formula (8)] were tested for solubility in water. Specifically, this test was performed by adding an excess amount of a given chromanol glycoside to 1 ml of water. The reaction mixture was incubated at 25° C. for 20 hours with constant stirring at 200 rpm. After 100 hours, the reaction mixture was transferred into a membrane filter (produced by Nihon Millipore Ltd. and marketed under trademark designation of "HPLC Sample Prep C02-LG") and insoluble substances were removed by centrifugation (4,100×g, 10 minutes, 20° C.). The filtered solution was subjected to HPLC to determine the amount of chromanol glycoside remaining in the aqueous solution. For the purpose of comparison, the 2-substituted alcohols represented by the aforementioned formulas (3) and (4) and Trolox were similarly tested.

The results of test are shown in Tables 5 and 6. It is clearly noted from the test results that the chromanol glycosides of this invention exhibit outstanding solubility in water. The numerals given in the tables represent the amounts of sample dissolved in 1 ml of water.

TABLE 5

|  | mg/ml |
|---|---|
| Chromanol glycoside of formula (4) of Example 1 | About 100 |
| Chromanol glycoside of formula (4) of Example 2 | About 1000 |
| Chromanol glycoside of formula (4) of Example 3 | About 1000 |
| Chromanol glycoside of formula (4) of Example 4 | About 1000 |
| Chromanol glycoside of formula (4) of Example 5 | About 1000 |
| Chromanol glycoside of formula (7) of Example 6 | 33 |
| Chromanol glycoside of formula (7) of Example 7 | 45 |
| Chromanol glycoside of formula (7) of Example 8 | 45 |

TABLE 6

|  | mg/ml |
|---|---|
| Chromanol glycoside of formula (5) of Example 4 | At least 10000 |
| Chromanol glycoside of formula (5) of Example 5 | At least 10000 |
| Chromanol glycoside of formula (8) of Example 8 | 141 |
| 2-Substituted alcohol of formula (3) | 1 |
| 2-Substituted alcohol of formula (6) | 0.1 |
| Trolox | 0.2 |

What is claimed is:

1. A chromanol glycoside represented by the formula (1):

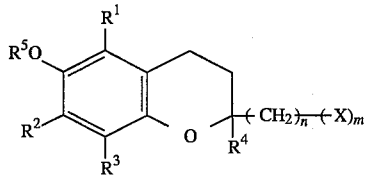

wherein $R^1$, $R^2$, $R^3$, and $R^4$ independently are selected from the group consisting of a hydrogen atom and a lower alkyl group, $R^5$ is selected from the group consisting of a hydrogen atom, a lower alkyl group, and a lower acyl group, X is selected from the group consisting of (1) a monosaccharide residue selected from the group consisting of pentose and hexose monosaccharide residues and (2) an oligosaccharide residue selected from the group consisting of oligopentose and oligohexose residues, in which monosaccharide and oligosaccharide residues the hydrogen atom of the hydroxyl group of the pentose or hexose residues may be replaced by a lower alkyl group or a lower acyl group, so as to provide the said residues with a substituent selected from the group consisting of free hydroxy groups, ether groups, and ester groups, n is in the range of 0 to 4, and m is an integer in the range of 1 to 6.

2. The chromanol glycoside according to claim 1, wherein m is an integer of 1 to 4.

3. The chromanol glycoside according to claim 1, wherein n is an integer of 0 to 2.

4. The chromanol glycoside according to claim 1, wherein said lower alkyl group and lower acyl group have 1 to 4 carbon atoms.

5. The chromanol glycoside according to claim 1, wherein $R^1$, $R^2$, $R^3$, and $R^4$ are methyl group and $R^5$ is hydrogen atom.

6. An antioxidant composition having an antioxidative effective amount of a chromanol glycoside represented by the formula (1):

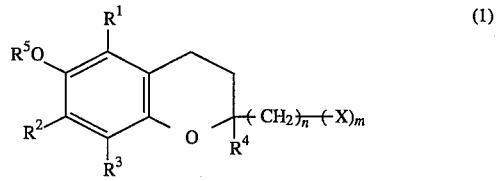

wherein $R^1$, $R^2$, $R^3$, and $R^4$ independently are selected from the group consisting of a hydrogen atom and a lower alkyl group, $R^5$ is selected from the group consisting of a hydrogen atom, a lower alkyl group, and a lower acyl group, X is selected from the group consisting of (1) a monosaccharide residue selected from the group consisting of pentose and hexose monosaccharide residues and (2) an oligosaccharide residue selected from the group consisting of oligopentose and oligohexose residues, in which monosaccharide and oligosaccharide residues the hydrogen atom of the hydroxyl group of the pentose or hexose residues may be replaced by a lower alkyl group or a lower acyl group, so as to provide the said residues with a substituent selected from the group consisting of free hydroxy groups, ether groups, and ester groups, n is in the range of 0 to 4, and m is an integer in the range of 1 to 6, and at least one additional component selected from the group consisting of water, alcohol, and buffer solution.

7. The antioxidant composition according to claim 6, wherein m is an integer of 1 to 4.

8. The antioxidant composition according to claim 6, wherein n is an integer of 0 to 2.

9. The antioxidant composition according to claim 6, wherein said lower alkyl group and lower acyl group have 1 to 4 carbon atoms.

10. The antioxidant composition according to claim 6, wherein $R^1$, $R^2$, $R^3$, and $R^4$ are methyl group and $R^5$ is hydrogen atom.

11. A method of preventing oxidation in a substrate comprising the step of applying to the substrate to be protected a compound according to claim 1.

12. A method of preventing oxidation in a substrate comprising the step of applying to the substrate to be protected a composition according to claim 6.

* * * * *

UNITED STATES PATENT AND TRADEMARK OFFICE
CERTIFICATE OF CORRECTION

PATENT NO. : 5,478,812
DATED : Dec. 26, 1995
INVENTOR(S) : Hironobu Murase, Tsutomu Kunieda, Tetsuya Tsujii It is certified that error appears in the above-indentified patent and that said Letters Patent is hereby corrected as shown below:

Column 6, line 33 (approx.): "]general" should read -- [general --.

Column 19, line 41: "EXAMPLE 10" should start a new paragraph.

Column 19, line 45: "(4)[," should read -- (4)], --.

Column 20, line 10 (approx.): "chroman-2" should read -- chroman-2- --.

Column 21, line 30 (approx.): "[6" should read -- [6- --.

Column 21, line 31: Delete "-" (dash) at the beginning of the line.

Column 23, line 10: "About 100" should read -- About 1000 --.

Signed and Sealed this

Twenty-sixth Day of March, 1996

Attest:

BRUCE LEHMAN

*Attesting Officer*     *Commissioner of Patents and Trademarks*